US012343103B2

(12) United States Patent
Oliver et al.

(10) Patent No.: US 12,343,103 B2
(45) Date of Patent: Jul. 1, 2025

(54) SYSTEMS AND METHODS FOR A KINEMATICALLY-CONTROLLED REMOTE CENTER MANIPULATOR

(71) Applicant: INTUITIVE SURGICAL OPERATIONS, INC., Sunnyvale, CA (US)

(72) Inventors: Ashley Lynne Oliver, Piedmont, CA (US); Ryan C. Abbott, San Jose, CA (US); Bram Gilbert Antoon Lambrecht, Redwood City, CA (US); John Ryan Steger, Los Gatos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 629 days.

(21) Appl. No.: 17/540,396

(22) Filed: Dec. 2, 2021

(65) Prior Publication Data
US 2022/0175480 A1    Jun. 9, 2022

Related U.S. Application Data

(60) Provisional application No. 63/120,851, filed on Dec. 3, 2020.

(51) Int. Cl.
*A61B 34/00* (2016.01)
(52) U.S. Cl.
CPC .................................. *A61B 34/70* (2016.02)
(58) Field of Classification Search
None
See application file for complete search history.

(56) References Cited

U.S. PATENT DOCUMENTS

| 2013/0184863 A1* | 7/2013 | Isobe | A61B 34/37 74/471 XY |
| 2013/0244820 A1* | 9/2013 | Solomon | B25J 18/00 474/58 |

(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — William J Levicky
*Assistant Examiner* — Willow Grace Welch
(74) *Attorney, Agent, or Firm* — Haynes & Boone, LLP

(57) ABSTRACT

A manipulator for articulating a surgical instrument may comprise an instrument holder configured to couple with the surgical instrument and to pivot about a remote center of motion. The manipulator may comprise a linkage assembly coupled to the instrument holder and configured to constrain rotational motion of the instrument holder to pivot about the remote center of motion. The linkage assembly may comprise a first, second, and third linkage arms. The second linkage arm may be rotatably coupled to the first linkage arm with a proximal end of the first linkage arm and a proximal end of the second linkage arm coupled at a proximal pivot joint. A third linkage arm may be translationally coupled to the second linkage arm. Movement of the second linkage arm and the third linkage arm may cause a distal end of the third linkage arm to trace an arc around the remote center of motion.

20 Claims, 21 Drawing Sheets

(56) References Cited

U.S. PATENT DOCUMENTS

2021/0030496 A1     2/2021  Devengenzo et al.
2022/0193890 A1*    6/2022  Castro .................... B25J 9/1065

* cited by examiner

SYSTEMS AND METHODS FOR A KINEMATICALLY-CONTROLLED REMOTE CENTER MANIPULATOR

CROSS-REFERENCE TO RELATED APPLICATIONS

This application claims the benefit of U.S. Provisional Application 63/120,851 filed Dec. 3, 2020, which is incorporated by reference herein in its entirety.

FIELD

The present disclosure is directed to systems and methods for robotically-assisted manipulation of an instrument about a kinematically-controlled remote center of motion using a manipulator adapted for space and weight constraints.

BACKGROUND

Minimally invasive medical techniques are intended to reduce the amount of tissue that is damaged during diagnostic or surgical procedures, thereby reducing patient recovery time, discomfort, and harmful side effects. Such minimally invasive techniques may be performed through one or more surgical incisions or through natural orifices in a patient anatomy. Through these incisions or natural orifices, clinicians may insert minimally invasive medical instruments (including surgical, diagnostic, therapeutic, or biopsy instruments) to reach a target tissue location. Minimally invasive robotically-assisted and computer-assisted medical systems have been developed to increase a surgeon's dexterity and avoid some of the limitations on traditional minimally invasive techniques. Robotically-assisted medical systems allow a user to control medical instruments via a manipulator. The manipulator may include two or more links coupled together by one or more joints. The joints may include actively controlled joints. The joints may also include passive joints, which are not actively controlled, but comply with movement of actively controlled joints. Such active and passive joints may be revolute or prismatic joints.

Minimally invasive telesurgical systems allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn control the motion of robotic instruments.

In some robotically-assisted medical systems, multiple manipulators may be mounted to a common platform which may be unwieldy or make some aspects of patient access difficult. For some medical procedures, more compact, more portable, and lighter weight manipulators may be suitable to improve patient access and procedure efficiency.

SUMMARY

Examples of the invention are summarized by the claims that follow the description.

Consistent with some examples, a manipulator for articulating a surgical instrument may comprise an instrument holder configured to couple with the surgical instrument and to pivot about a remote center of motion. The manipulator may comprise a linkage assembly coupled to the instrument holder and the manipulator may be configured to constrain rotational motion of the instrument holder to pivot about the remote center of motion. The linkage assembly may comprise a first, second, and third linkage arms. The second linkage arm may be rotatably coupled to the first linkage arm with a proximal end of the first linkage arm and a proximal end of the second linkage arm coupled at a proximal pivot joint. A third linkage arm may be translationally coupled to the second linkage arm. Movement of the second linkage arm and the third linkage arm may cause a distal end of the third linkage arm to trace an arc around the remote center of motion.

In another example, a manipulator for articulating a surgical instrument may comprise an instrument holder configured to couple with the surgical instrument and to pivot through a remote center of motion and may comprise a linkage assembly coupled to the instrument holder and configured to constrain motion of the instrument holder to pivot about the remote center of motion. The linkage assembly may comprise a proximal pivot joint, a distal pivot joint and an extension joint between the proximal pivot joint and the distal pivot joint. A motor may drive at least one of coupled motion of the proximal pivot joint and the extension joint and coupled motion of the extension joint and the distal pivot joint.

In another example, a manipulator for articulating a surgical instrument may comprise an instrument holder configured to couple with the surgical instrument and to pivot about a remote center of motion. The manipulator may also comprise a linkage assembly coupled to the instrument holder and configured to constrain motion of the instrument holder to pivot about the remote center of motion. The linkage assembly may comprise a first linkage arm having a guide, a second linkage arm rotatably coupled to the first linkage arm, and a third linkage arm translationally coupled to the second linkage arm and configured to travel along the guide of the first linkage arm. The movement of the second linkage arm and the third linkage arm may cause a distal end of the third linkage arm to trace an arc around the remote center of motion.

In another example, a method of operating a manipulator that includes a translation linkage arm, a pivot linkage arm and a base linkage arm, may comprise translating the translation linkage arm relative to the pivot linkage arm and the base linkage arm. The base linkage arm may include a guide. A follower coupled to the translation linkage arm may be configured to move within the track of the base linkage arm. The pivot linkage arm may be coupled to the base linkage arm by a proximal pivot joint. The method may also comprise pivoting the pivot linkage arm and the translation linkage arm relative to the base linkage arm about the proximal pivot joint as the follower moves within the guide of the base linkage arm. The method may also comprise tracing an arc around a remote center of motion of the manipulator with the distal end of the translation linkage arm and rotating an instrument holder about the remote center of motion of the manipulator.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Figure 1A:
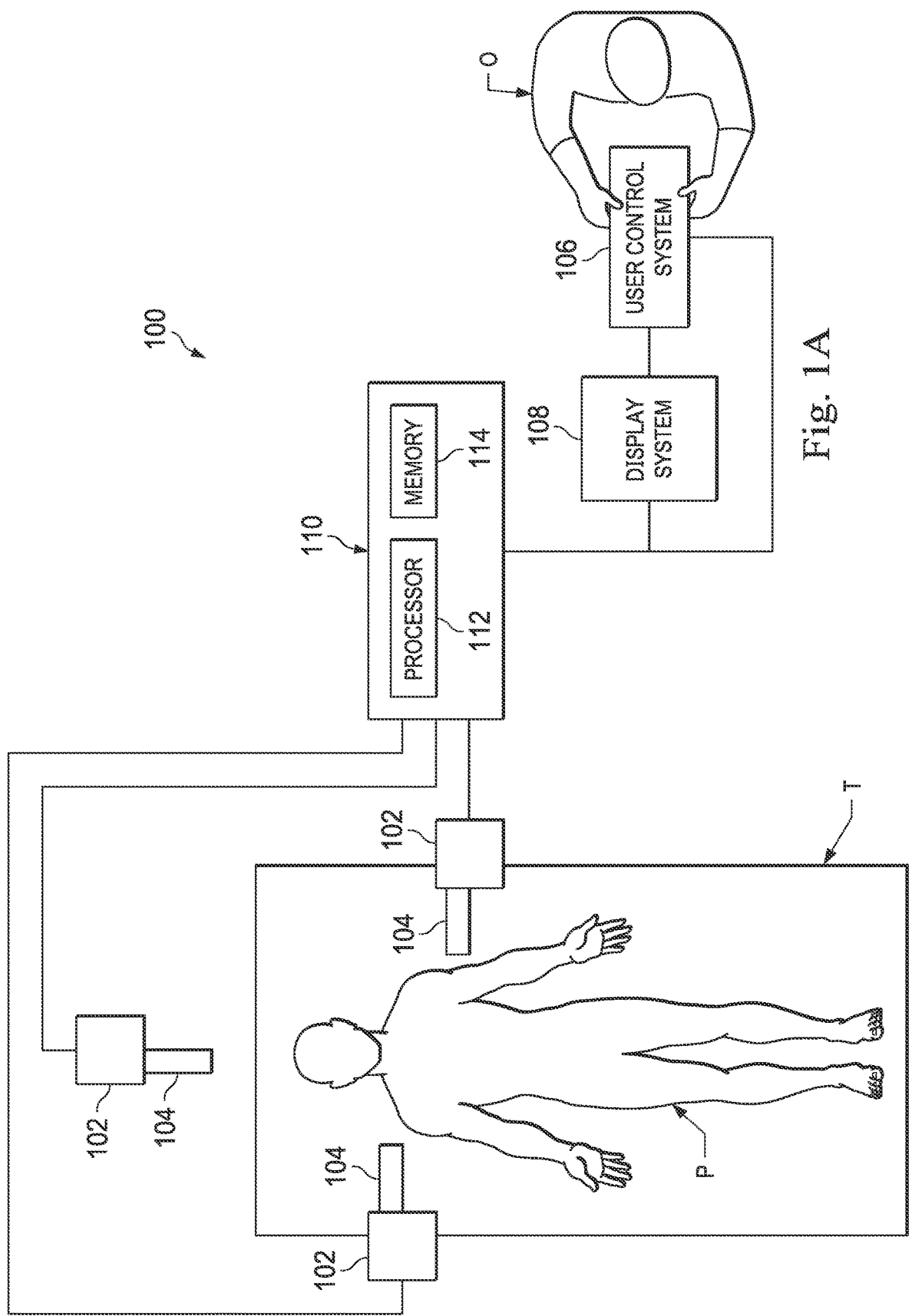
FIG. 1A is a simplified diagram of a robotically-assisted medical system according to some embodiments.

Embodiments of the present disclosure and their advantages are best understood by referring to the detailed description that follows. It should be appreciated that like reference numerals are used to identify like elements illustrated in one or more of the figures for purposes of illustrating but not limiting embodiments of the present disclosure.

DETAILED DESCRIPTION

The present disclosure describes various systems and instruments in terms of their state in three-dimensional space. As used herein, the term position refers to the location of an object or a portion of an object in a three-dimensional space (e.g., three degrees of translational freedom along Cartesian X-, Y-, and Z-coordinates). As used herein, the term orientation refers to the rotational placement of an object or a portion of an object (e.g., three degrees of rotational freedom, such as roll, pitch, and yaw). Further, as used herein, the term "distal" means a location closer to a surgical site and the term "proximal" means a location farther away from the surgical site, unless otherwise indicated.

FIG. 1A is a simplified diagram of a robotically-assisted medical system 100 according to some embodiments. In some embodiments, system 100 may be suitable for use in therapeutic and diagnostic procedures. While some embodiments are provided herein with respect to such procedures, any reference to medical or surgical instruments and medical or surgical methods is non-limiting. The systems, instruments, and methods described herein may be used for animals, human cadavers, animal cadavers, portions of human or animal anatomy, non-surgical diagnosis, as well as for industrial systems and general robotic, general teleoperational, or robotic medical systems. For example, the systems, instruments, and methods described herein may be used for non-medical purposes including industrial uses, general robotic uses, and manipulating non-tissue work pieces.

As shown in FIG. 1A, system 100 generally includes a plurality of manipulator assemblies 102. Although three manipulator assemblies 102 are illustrated in the embodiment of FIG. 1A, in other embodiments, more or fewer manipulator assemblies may be used. The exact number of manipulator assemblies will depend on the medical procedure and the space constraints within the operating room, among other factors.

The manipulator assembly 102 is used to operate a medical instrument 104 (e.g., a surgical instrument or an image capturing device) in performing various procedures on a patient P. The manipulator assembly 102 may be teleoperated, non-teleoperated, or a hybrid teleoperated and non-teleoperated assembly with select degrees of freedom of motion that may be motorized and/or teleoperated and select degrees of freedom of motion that may be non-motorized and/or non-teleoperated. Manipulator assembly 102 is mounted to or located near an operating or surgical table T. In various embodiments, manipulator assembly 102 may be rigidly mounted to the table T, to a cart placed near the table T, to a floor stand, or to the ceiling of the operating room. In embodiments in which a plurality of manipulator assemblies 102 are employed, one or more of the manipulator assemblies 102 may support surgical instruments, and another of the manipulator assemblies 102 may support an image capturing device, such as a monoscopic or stereoscopic endoscope.

A user control system 106 allows an operator (e.g., a surgeon or other clinician as illustrated in FIG. 1A) to view the interventional site and to control manipulator assembly 102. In some examples, the user control system 106 is a surgeon console, which is usually located in the same room as the operating or surgical table T, such as at the side of a table on which patient P is located. It is to be understood, however, that operator O can be located in a different room or a completely different building from patient P. That is, one or more user control systems 106 may be collocated with the manipulator assemblies 102, or the user control systems may be positioned in separate locations. Multiple user control systems allow more than one operator to control one or more robotically-assisted manipulator assemblies in various combinations.

User control system 106 generally includes one or more input devices for controlling manipulator assembly 102. The input devices may include any number of a variety of devices, such as joysticks, trackballs, data gloves, trigger-guns, hand-operated controllers, voice recognition devices, body motion or presence sensors, and/or the like. To provide operator O a strong sense of directly controlling medical instrument 104, the input devices may be provided with the same degrees of freedom as the associated medical instrument 104. In this manner, the input devices provide operator O with telepresence and the perception that the input devices are integral with medical instrument 104.

Manipulator assembly 102 supports medical instrument 104 and may include a kinematic manipulator support structure of one or more non-servo controlled linkages (e.g., one or more links that may be manually positioned and locked in place), and/or one or more servo controlled linkages (e.g., one or more links that may be controlled in response to commands from a control system), and an instrument holder. Manipulator assembly 102 may optionally include a plurality of actuators or motors that drive inputs on medical instrument 104 in response to commands from the control system (e.g., a control system 110). The actuators may optionally include drive systems that when coupled to medical instrument 104 may advance medical instrument 104 into a naturally or surgically created anatomic orifice. Other drive systems may move the distal end of medical instrument 104 in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the actuators can be used to actuate an articulable end effector of medical instrument 104 for grasping tissue in the jaws of a biopsy device and/or the like. Actuator position sensors such as resolvers, encoders, potentiometers, and other mechanisms may provide sensor data to system 100 describing the rotation and orientation of the motor shafts. This position sensor data may be used to determine motion of the objects manipulated by the actuators. The manipulator assembly 102 may position its held instrument 104 so that a pivot point occurs at the instrument's entry aperture into the patient. The pivot point may be referred to as a remote center of motion. The manipulator assembly 102 may then manipulate its held instrument so that the instrument may be pivoted about the remote center of motion, inserted into and retracted out of the entry aperture, and rotated about its shaft axis.

System 100 also includes a display system 108 for displaying an image or representation of the surgical site and medical instrument 104. Display system 108 and user control system 106 may be oriented so operator O can control medical instrument 104 and user control system 106 with the perception of telepresence. In some examples, the display system 108 may present images of a surgical site recorded pre-operatively or intra-operatively using image data from imaging technology such as, computed tomography (CT), magnetic resonance imaging (MRI), fluoroscopy, thermography, ultrasound, optical coherence tomography (OCT), thermal imaging, impedance imaging, laser imaging, nanotube X-ray imaging, and/or the like.

System 100 also includes control system 110. Control system 110 includes at least one memory 114 and at least one computer processor 112 for effecting control between medical instrument 104, user control system 106, and display system 108. Control system 110 also includes programmed instructions (e.g., a non-transitory machine-readable medium storing the instructions) to implement some or all of the methods described in accordance with aspects disclosed herein, including instructions for providing information to display system 108. While control system 110 is shown as a single block in the simplified schematic of FIG. 1, the system may include two or more data processing circuits with one portion of the processing optionally being performed on or adjacent to manipulator assembly 102, another portion of the processing being performed at user control system 106, and/or the like. The processors of control system 110 may execute instructions corresponding to processes disclosed herein and described in more detail below. Any of a wide variety of centralized or distributed data processing architectures may be employed. Similarly, the programmed instructions may be implemented as a number of separate programs or subroutines, or they may be integrated into a number of other aspects of the robotic medical systems described herein. In one embodiment, control system 110 supports wireless communication protocols such as Bluetooth, IrDA, HomeRF, IEEE 802.11, DECT, and Wireless Telemetry.

Movement of a manipulator assembly 102 may be controlled by the control system 110 so that a shaft or intermediate portion of instruments mounted to the manipulator assemblies 102 are constrained to safe motions through minimally invasive surgical access sites or other apertures. Such motion may include, for example, axial insertion of a shaft through an aperture site, rotation of the shaft about its axis, and pivotal motion of the shaft about a pivot point adjacent the access site. In some cases, excessive lateral motion of the shaft that might otherwise tear the tissues adjacent the aperture or enlarge the access site inadvertently is inhibited. Some or all of such constraint on the motions of the manipulator assemblies 102 at the access sites may be imposed using mechanical manipulator joint linkages that inhibit improper motions or may in part or in full be imposed using data processing and control techniques. In some embodiments, control system 110 may receive force and/or torque feedback from medical instrument 104. Responsive to the feedback, control system 110 may transmit signals to user control system 106. In some examples, control system 110 may transmit signals instructing one or more actuators of manipulator assembly 102 to move medical instrument 104.

Figure 1B:
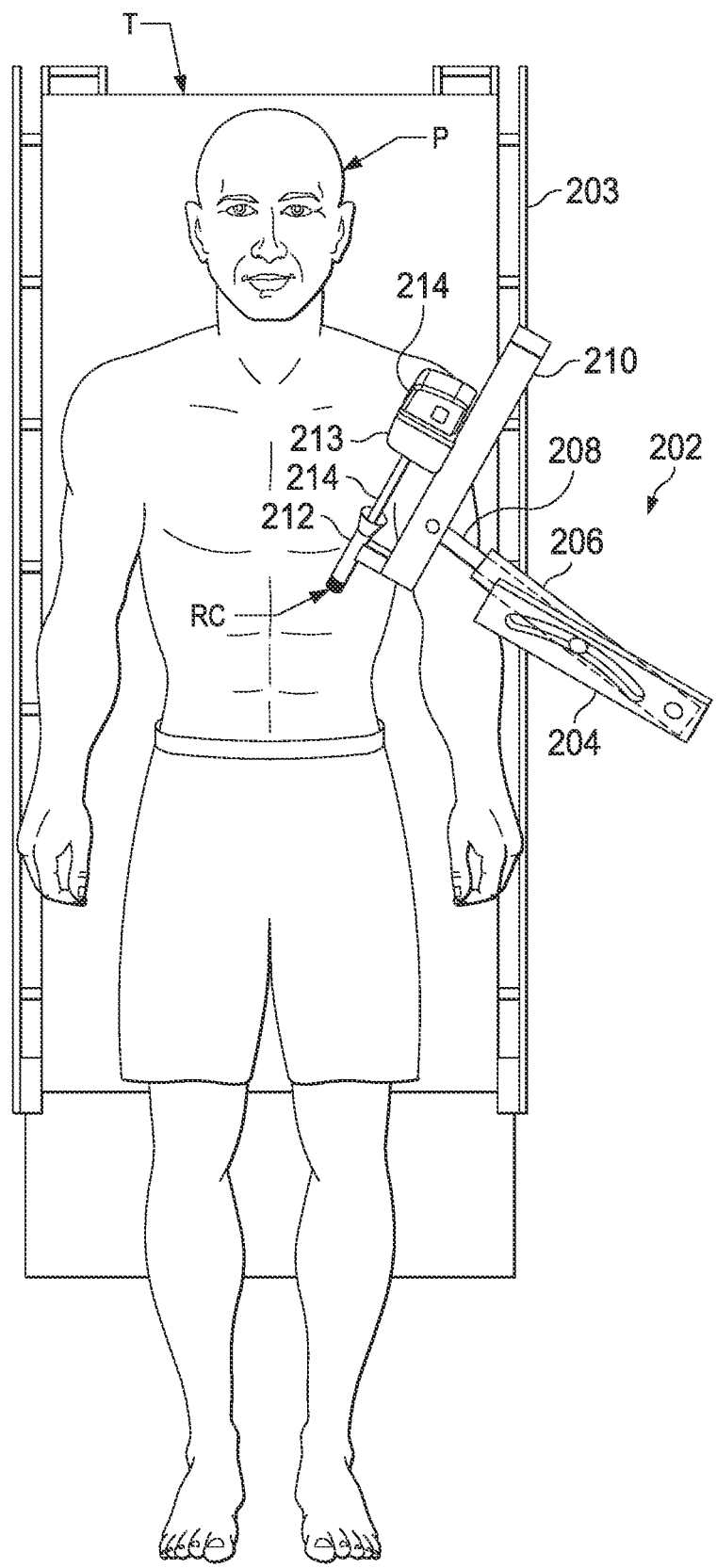
FIG. 1B illustrates a manipulator assembly mounted to a surgical table according to some embodiments.

FIG. 1B illustrates a manipulator assembly 202 mounted to a side rail 203 of the surgical table T according to some embodiments. In alternative embodiments, the manipulator assembly 202 may be mounted to a cart placed near the table T, to a floor stand, or to the ceiling of the operating room. The manipulator assembly 202 may be used as the manipulator assembly 102 described above. In this embodiment, the manipulator assembly 202 includes a base linkage arm 204 (e.g., a first linkage arm) rotatably coupled to a pivot linkage arm 206 (e.g., a second linkage arm). The base linkage arm 204 may be coupled to the table T via one or more manually positionable linkages and/or one or more servo controlled linkages. A translation linkage arm 208 (e.g., a third linkage arm) is movably coupled to the pivot linkage arm 206 such that the translation linkage 208 may translate with respect to the pivot linkage arm 206. A distal end of the translation linkage arm 208 is rotatably coupled to a distal linkage arm 210 (e.g., a fourth linkage arm). The distal linkage arm 210 may include or be coupled to an instrument holder configured to support and actuate a detachable medical instrument 214 during a medical procedure. By way of example, the medical instrument 214 may be a therapeutic surgical instrument, an endoscopic camera, etc., and may be used as the medical instrument 104 of FIG. 1A. Referring to FIGS. 1A and 1B together, the manipulator assembly 202 and the medical instrument 214 may communicate with the system 100 through the control system 110. The instrument holder may include a carriage 213 configured for mounting the instrument to the manipulator assembly 202. The carriage 213 may be slidingly associated with the distal linkage arm 210 to translate the instrument 214 with respect to the distal linkage arm 210. The carriage 213 may include one or more motors or actuators for actuating components of the instrument (e.g., articulation and/or manipulation of an end effector of the instrument). In addition, the distal linkage arm 210 may be configured to retain a cannula 212 near an end portion of the distal linkage arm 210. The cannula 212 may be part of the instrument holder, and may be spaced apart from the carriage 213 as shown in FIG. 1B. The cannula may be used to provide an interface between a surgical opening in the patient P and the medical instrument 214 during a medical procedure. The cannula 212 may be removably coupled to the distal linkage arm 210 such that the cannula 212 is rigidly mounted to the distal linkage arm 210 when attached, and the cannula 212 may be separated from the distal linkage arm 210, for example, for sterilization. An opening in the cannula 212 is sized for passage of a shaft of the instrument 214 through the opening for insertion of a distal (toward the patient) portion of the instrument 214 into the patient P.

The manipulator assembly 202 may position its held instrument 214 so that a pivot point occurs at the instrument's 214 entry aperture into the patient P. The pivot point may be referred to as a remote center of motion RC. The manipulator assembly 202 may then manipulate its held instrument 214 so that the instrument 214 may be pivoted about the remote center of motion RC, inserted into and retracted out of the entry aperture, and rotated about its shaft axis. During a procedure, the remote center of motion RC remains fixed by the manipulator assembly 202 such that the instrument 214 and the instrument holder (e.g., the cannula 212 and the motor carriage 213) are able to pivot about the remote center of motion RC, but do not translate transversely relative to the remote center of motion RC. Thus, the instrument holder (e.g., the cannula 212 and the motor carriage 213) may be constrained in rotational motion to pivoting about the remote center of motion RC while the carriage 213 is further constrained to an insertion motion along an insertion axis along the distal linkage arm 210. In some traditional embodiments, hardware-constrained, robotically-assisted manipulators have included long kinematic chains with heavy linkage arms and expansive sweeps to move the instrument through large spatial volumes about the remote center. These large, heavy linkage arms may occlude the view of clinical staff, crowd the area around the patient P and the remote center of motion RC, and require large, heavy bases to serve as ballast. In other traditional embodiments, software-constrained, robotically-assisted manipulators have included individually-controlled motors at each joint in the kinematic chain of the manipulator to control movement of the instrument about the remote center. In these embodiments, the manipulator may be heavy and stiff due to the motors positioned along the kinematic chain and may have difficulty choreographing joint motion. The embodiments described herein may allow for smaller, more lightweight manipulators and linkage assemblies that allow for better access to the patient, as compared to traditional manipulators.

Figure 2:
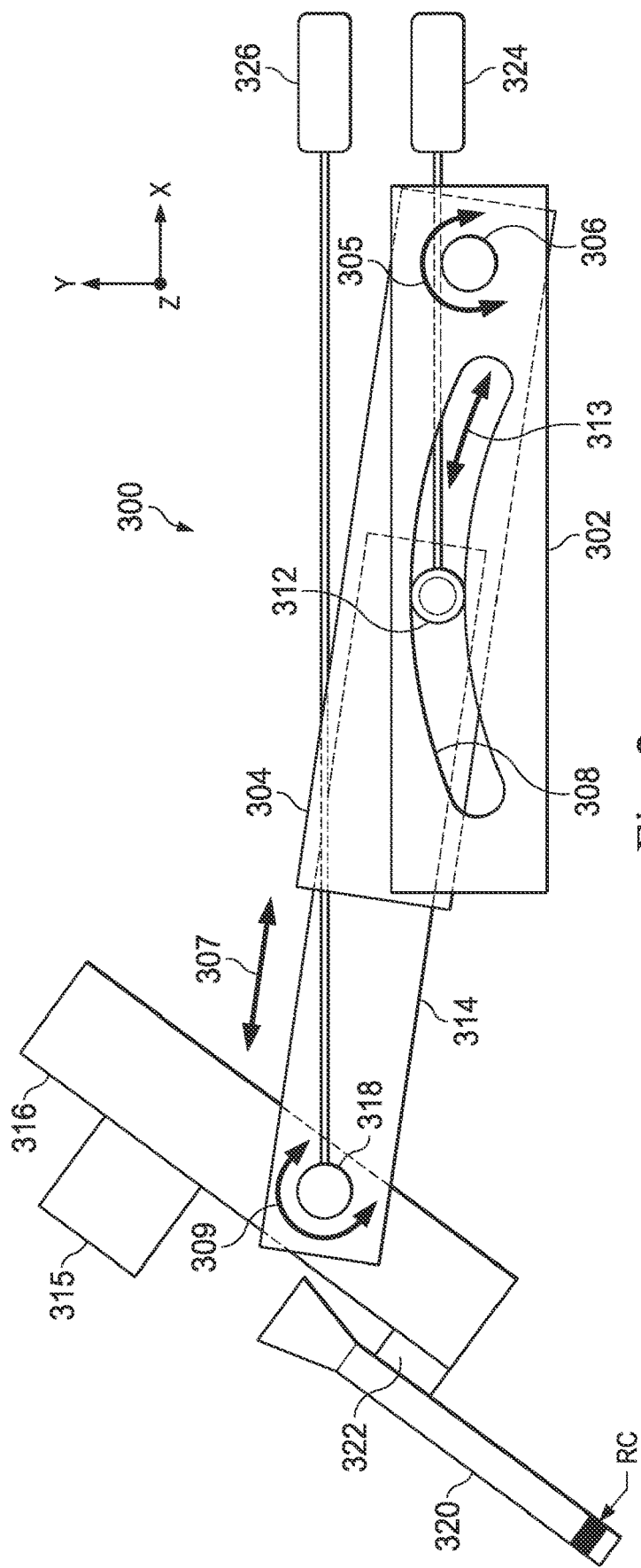
FIG. 2 is a schematic view of a manipulator assembly according to some embodiments.

FIG. 2 provides a schematic view of a manipulator assembly 300 in a manipulator frame of reference having a Cartesian coordinate system (X, Y, Z) according to some embodiments. The manipulator assembly 300 may be used as the manipulator assembly 102/202 described above. In this embodiment, a linkage assembly includes a base linkage arm 302 (e.g., a first linkage arm), a pivot linkage arm 304 (e.g., a second linkage arm), a translation linkage arm 314 (e.g., a third linkage arm), and a distal linkage arm 316 (e.g., a fourth linkage arm). The base linkage arm 302 may be coupled to the table T, to a cart placed near the table T, to a floor stand, to the ceiling of the operating room, or otherwise mounted within a surgical environment. The base linkage arm 302 may be mounted (e.g., to the table T) via one or more manually positionable linkages and/or one or more servo-controlled linkages that are proximal to the base linkage arm 302. The base linkage arm 302 may be rotationally coupled to a more proximal linkage via a yaw joint. The yaw joint may rotationally couple a proximal end of the base linkage arm 302 to the distal end of the more proximal linkage. The yaw joint may be driven by an actuation mechanism, for example, an actuator such as an electric motor, a hydraulic actuator, or an pneumatic actuator and a gear assembly or other mechanical assembly to control the direction and speed of the output of the actuator. The yaw joint is operable to produce controlled rotation (e.g., roll) of the base linkage arm 302 about a yaw axis that intersects the remote center of motion RC, the rotation corresponding to motion about the YZ plane in the orientation in FIG. 2. As such, the base linkage arm 302 has a center of rotation passing through the remote center of motion RC. Because the distal linkage arm 316 and mounted surgical instrument (when present) are coupled to the base linkage arm 302 via the intervening linkage components of the manipulator assembly 300, rotation (roll) of the base linkage arm 302 about the yaw axis generates corresponding rotation of the distal linkage arm 316 and mounted surgical instrument about the yaw axis, thereby maintaining the position and orientation of the remote center of motion RC for all angular orientations of the yaw joint. The term "yaw" is arbitrary, and under this term it can be seen that with the remote center of motion RC stationary, rotation around yaw axis will cause the distal tip of surgical instrument to move in a way defined as yaw.

The base linkage arm 302 may be coupled to the pivot linkage arm 304 by a proximal pivot joint 306 such that the pivot linkage arm 304 moves with a rotational motion 305 about the pivot joint 306 in an XY plane relative to the orientation shown in FIG. 2. As shown in FIG. 2, a proximal end of the base linkage arm 302 and a proximal end of the pivot linkage arm 304 may be coupled at the proximal pivot joint 306. The base linkage arm 302 may include a guide or track 308. In some embodiments, the track 308 may be a cam race. The track 308 may have a curvilinear shape. In some embodiments, the track 308 may be, for example, a curvilinear slot. The translation linkage arm 314 may be coupled to the base linkage arm 302 by a follower 312 (e.g., a cam follower) that is coupled to a proximal end of the translation linkage arm 314. The follower 312 may be positioned in and may be constrained by the track 308 to travel along a curvilinear path 313 defined by the track 308. The translation linkage arm 314 may also be translatably coupled (e.g., telescoping, sliding) to the pivot linkage arm 304 to have a translational motion 307 in the XY plane. Rotational motion between the pivot linkage arm 304 and the translation linkage arm 314 may be restricted. As the translation linkage arm 314 is extended or retracted with the translation motion 307, the follower 312 within the track 308 may cause the pivot linkage arm 304 and the translation linkage arm 314 to pivot together with the rotation motion 305 as the follower 312 moves along the curvilinear shape of the track 308. In other words, a single motor or actuator may be used to actuate both the translational motion 307 and the rotational motion 305. A distal end of the translation linkage arm 314 may be rotatably coupled to the distal linkage arm 316 by a distal pivot joint 318 such that the distal linkage arm 316 moves with a rotational motion 309 about the pivot joint 318 in the XY plane. The distal linkage arm 316 may include or be coupled to an instrument holder configured to support and articulate a detachable instrument. The instrument holder may include a carriage 315 configured for mounting the instrument to the manipulator assembly 300. The carriage 315 may be slidingly associated with the distal linkage arm 316 to translate the instrument with respect to the distal linkage arm 316. The carriage 315 may also include one or more motors or actuators for actuating components of the instrument (e.g., articulation and/or manipulation of an end effector of the instrument). A cannula 320 may be removably coupled to a distal end of the distal linkage arm 316 by a clamp 322. The cannula 320 may be part of the instrument holder and may be spaced apart from the carriage 315 as shown in FIG. 2. The cannula 320 may have an inner channel sized to receive a shaft of the instrument through the channel. As the linkage arms 302, 304, 314, and 316 are moved, the carriage 315, cannula 320, and mounted instrument may be constrained to move in an XY plane about a remote center of motion RC fixed in the XY plane. Thus, the instrument holder (e.g., the cannula 320 and the motor carriage 315) may be constrained in rotational motion to pivoting about the remote center of motion RC while the carriage 315 is further constrained to an insertion motion along an insertion axis along the distal linkage arm 316.

The translational motion 307 of the translation linkage arm 314 with respect to the pivot linkage arm 304 may be driven by an actuation mechanism 324 including, for example, an actuator such as an electric motor, a hydraulic actuator, or an pneumatic actuator and a gear assembly or other mechanical assembly to control the direction and speed of the output of the actuator. The actuation mechanism 324 may be controlled by a control system (e.g., control system 110). Because the rotational motion 305 and the translational motion 307 are coupled, the actuation mechanism may cause both the rotational motion 305 and the translational motion 307 to be moved by a single motor or actuator. The translational motion 307 may be driven by a motor or actuator of the actuation mechanism 324, and the rotational motion 305 may also be pivoted as a function of the translational motion 307 (e.g., the amount of rotational motion 305 may be a function of the amount of driven translational motion 307). Thereby, a separate motor or actuator would not be required to drive the rotational motion 305.

The rotational motion 309 of the distal linkage arm 316 with respect to the translation linkage arm 314 may be driven by a distal pivot motion mechanism 326. In some embodiments, the distal pivot motion mechanism 326 may include, for example, an actuator such as an electric motor, a hydraulic actuator, or a pneumatic actuator and may include a gear assembly or other mechanical assembly to control the direction and speed of the output of the actuator. In this embodiment, the distal pivot motion 309 may be controlled independently of the proximal pivot/translational motion by the second actuator. The distal pivot motion mechanism 326 may be controlled by the control system (e.g., control system 110). In other embodiments, the distal pivot motion mechanism 326 may include a link assembly that is coupled to the actuator of the actuation mechanism 324 such that a single actuator controls the proximal pivot motion 305, the translation motion 307 and the distal pivot motion 309.

In various alternative embodiments, a single actuation mechanism may drive coupled motion of the system joints. For example, a single actuation mechanism may drive rotational motion 305, translational motion 307, and distal pivot motion 309. In various alternative embodiments, the actuation mechanism 326 may drive coupled motion of the translational motion 307 and distal pivot motion 309, while the actuation mechanism 324 drives only the rotational motion 305.

Figure 3:
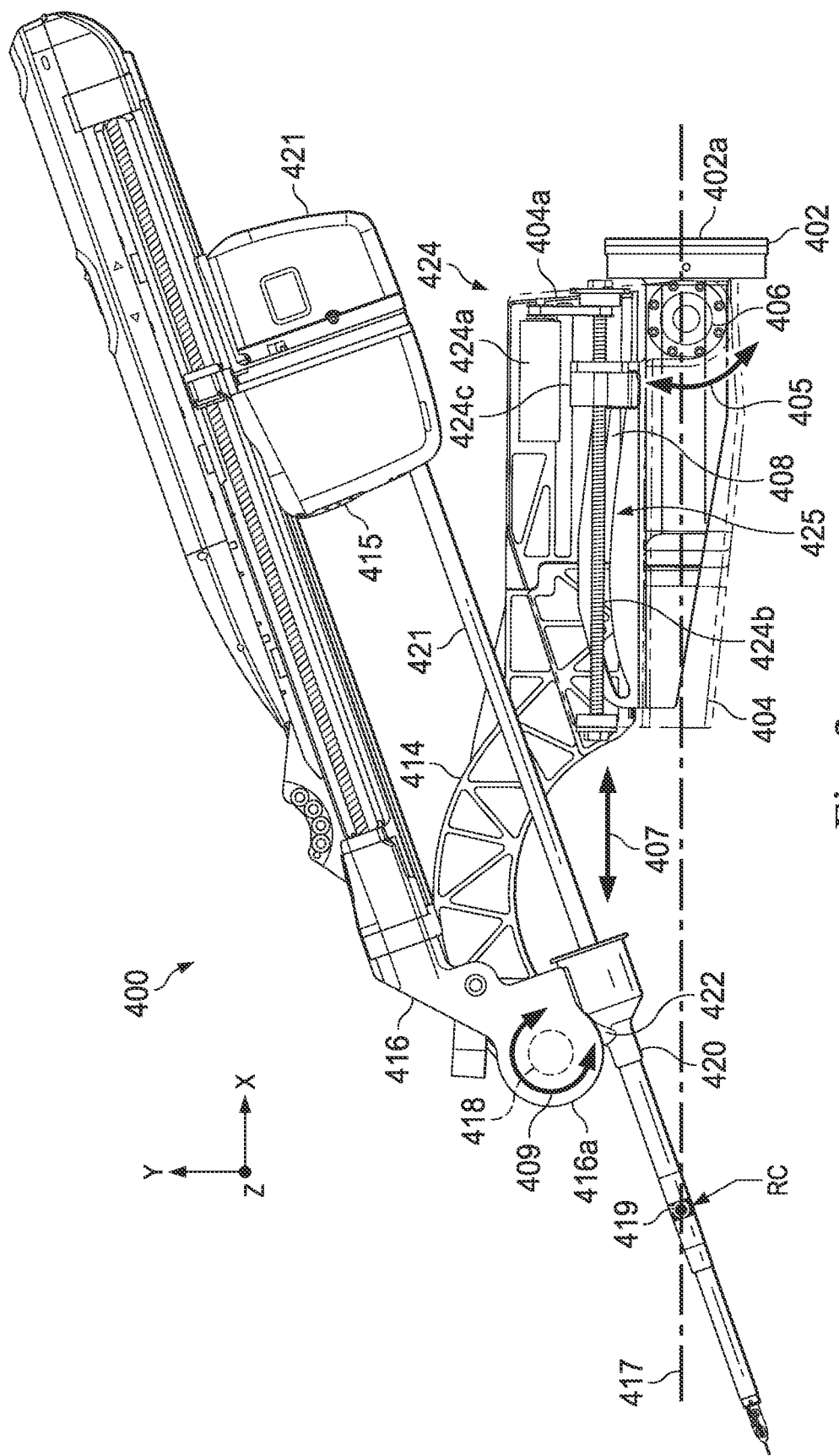
FIG. 3 is a side view of a manipulator assembly in a retracted configuration according to some embodiments.
Figure 4:
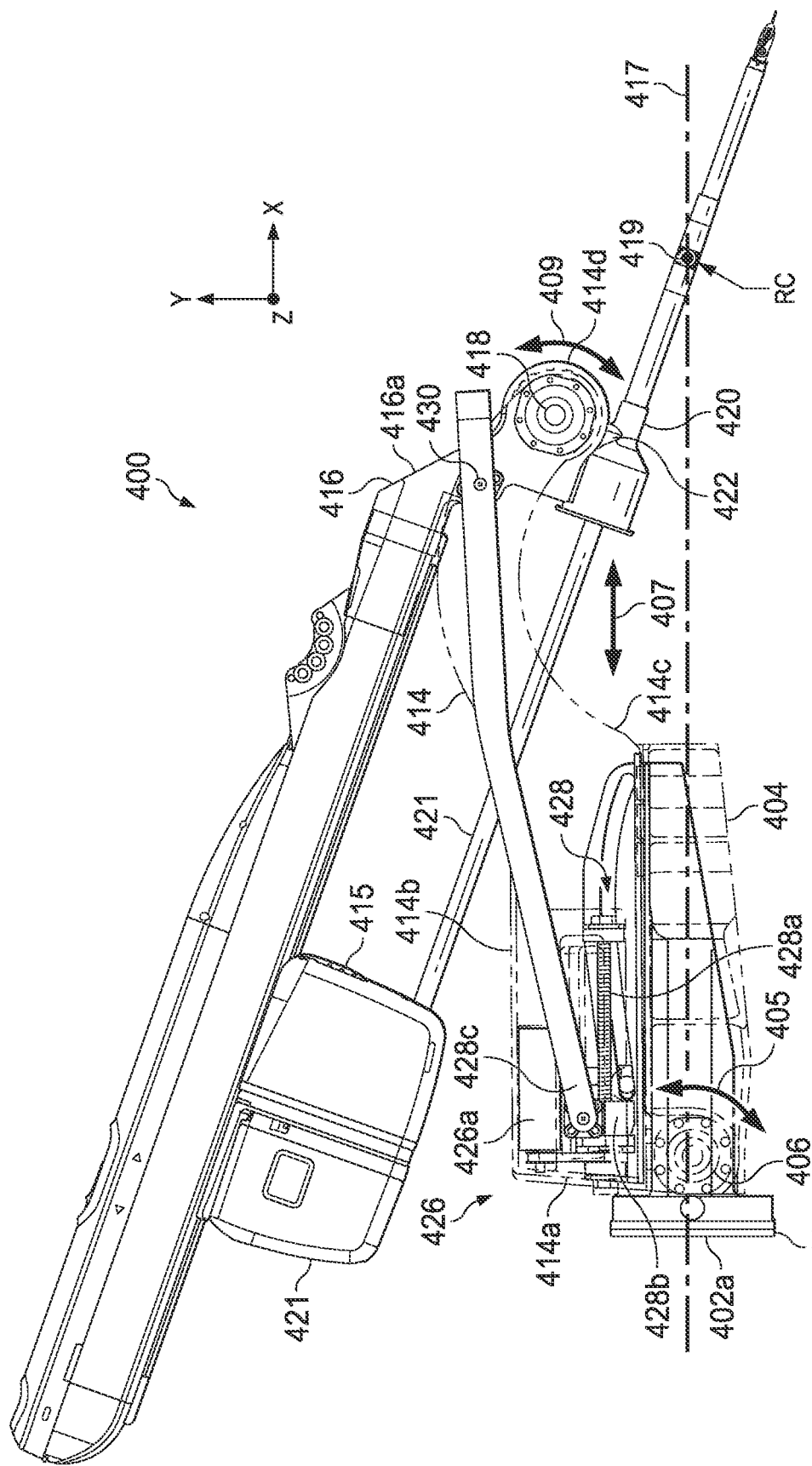
FIG. 4 is an opposite side view of the manipulator assembly of FIG. 3 in the retracted configuration according to some embodiments.
Figure 5:
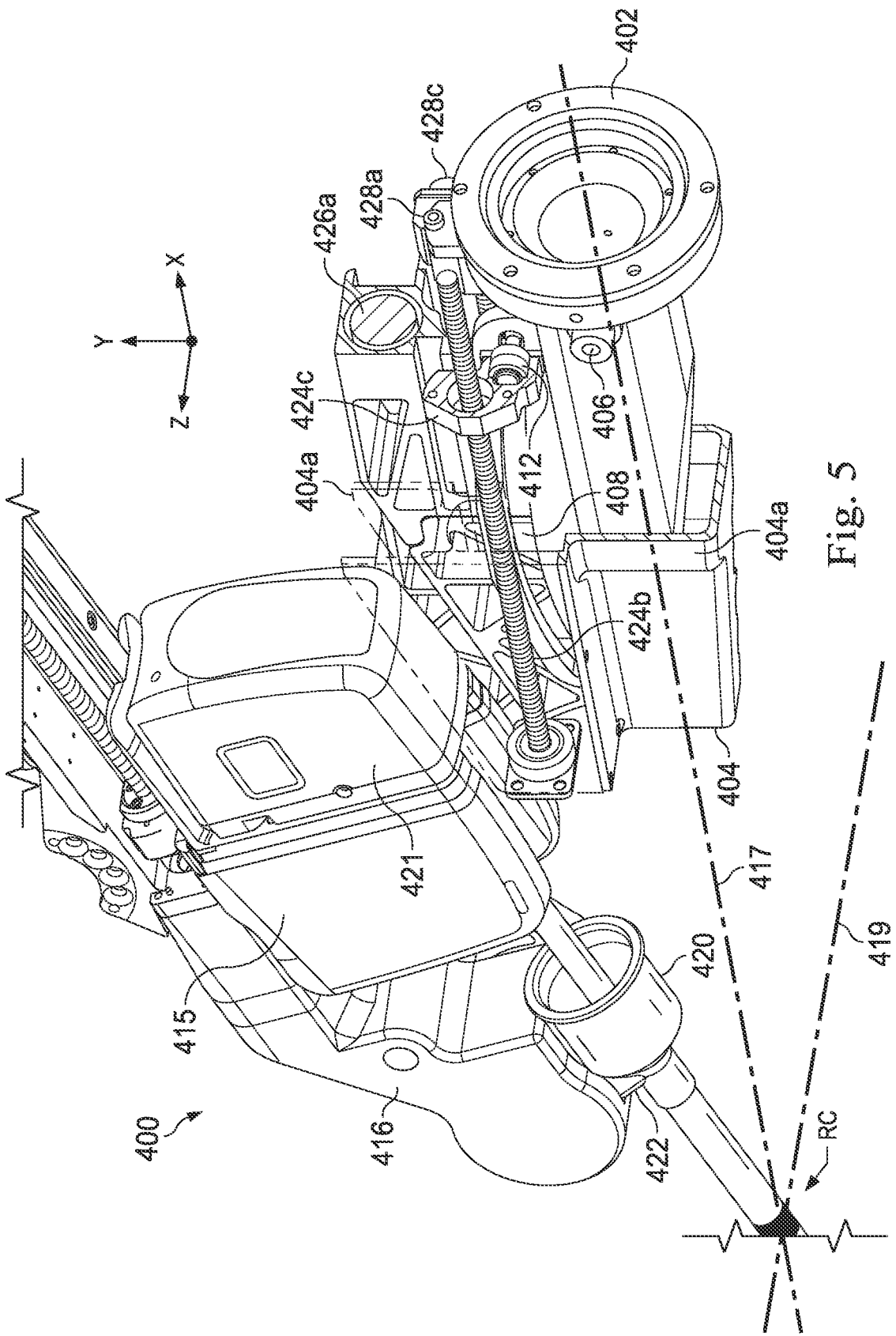
FIG. 5 is a perspective view of a portion of the manipulator assembly of FIG. 3 in the retracted configuration according to some embodiments.

FIGS. 3-11 illustrate a manipulator assembly 400 in a manipulator frame of reference having a Cartesian coordinate system (X, Y, Z) according to some embodiments. The manipulator assembly 400 may be used as the manipulator assembly 102/202/300 described above. FIGS. 3-5 illustrate the manipulator assembly 400 in a retracted configuration. FIG. 3 provides a side view of the manipulator assembly 400, and FIG. 4 provides the opposite side view of the manipulator assembly. FIG. 5 provides a perspective, cut-away view a portion of the manipulator assembly 400. In this embodiment, a base linkage arm 402 (e.g., a first linkage arm) may be coupled to a pivot linkage arm 404 (e.g., a second linkage arm) by a proximal pivot joint 406 such that the pivot linkage arm 404 moves in a rotation motion 405 about the pivot joint 406 in the XY plane relative to the orientations in FIGS. 3-5. A proximal end of the base linkage arm 402 and a proximal end of the pivot linkage arm 404 may be coupled at the proximal pivot joint 406. The base linkage arm 402 may include a guide or track 408. In some embodiments, the track 408 may be a cam race and may have a curvilinear shape. The track may be, for example, a curvilinear slot. The pivot linkage arm 404 may include a housing 404a. In some embodiments, a proximal flange 402a of the base linkage arm 402 may be fixed to the table T or other structure held stationary during the medical procedure. In other embodiments, the base linkage arm 402 may be rotationally coupled to a more proximal linkage via a yaw joint. The yaw joint may rotationally couple a proximal end of the base linkage arm 402 to the distal end of the more proximal linkage. The yaw joint may be driven by an actuation mechanism, for example, an actuator such as an electric motor, a hydraulic actuator, or an pneumatic actuator and a gear assembly or other mechanical assembly to control the direction and speed of the output of the actuator. The yaw joint is operable to produce controlled rotation (roll) of the base linkage arm 402 about a yaw axis 417 that intersects the remote center of motion RC, the rotation corresponding to motion about the YZ plane in the orientations in FIGS. 3-11. The rotation of the base linkage arm 402 about the yaw axis 417 causes corresponding yaw motion of the portions of the manipulator assembly 400 distal to the base linkage arm 402, while maintaining the remote center of motion RC.

Figure 6:
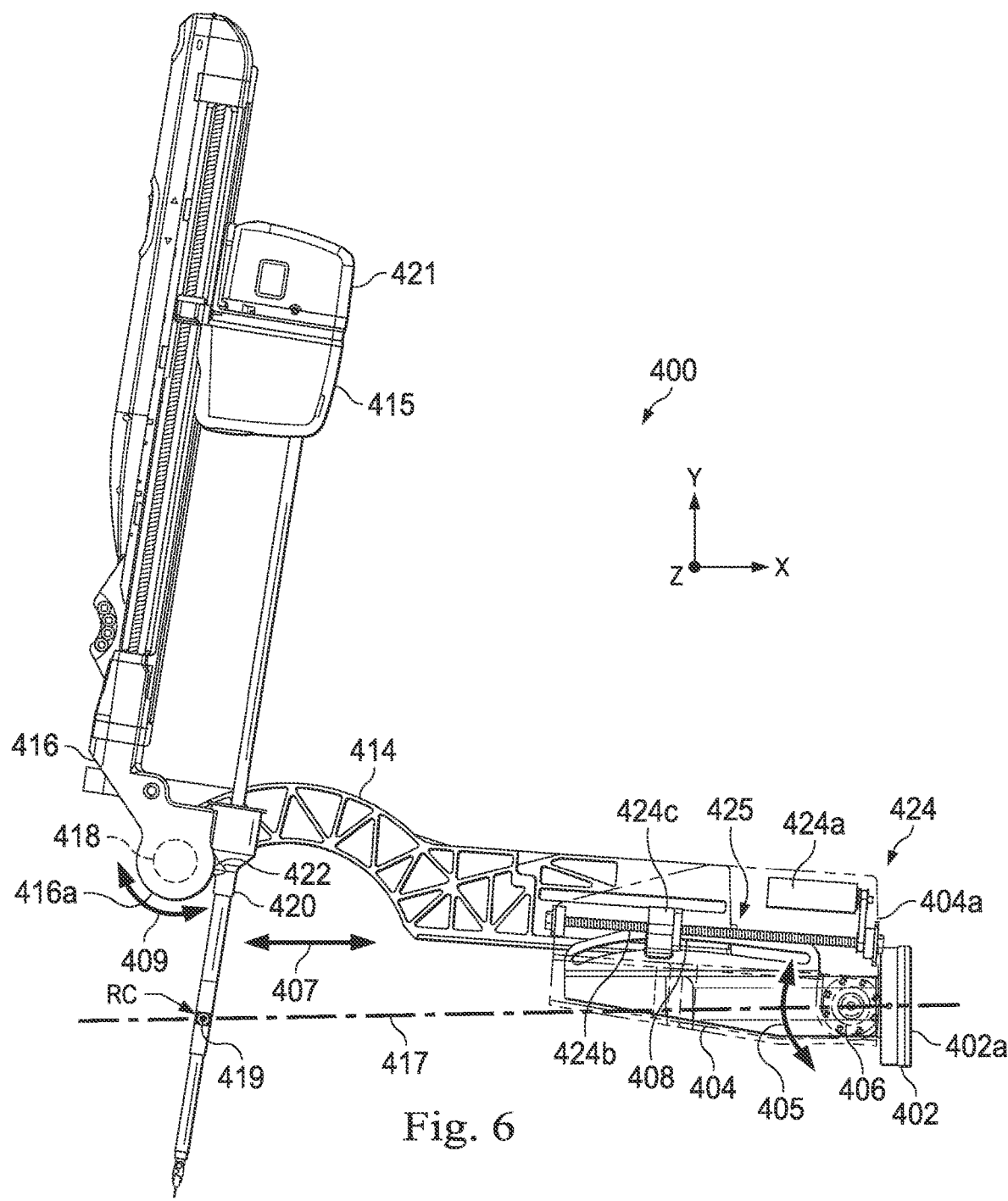
FIG. 6 is a side view of the manipulator assembly of FIG. 3 in a partially extended or mid-extension configuration according to some embodiments.

A translation linkage arm 414 (e.g., a third linkage arm) may be coupled to the base linkage arm 402 by a follower 412 (e.g., a cam follower) that is coupled to a proximal end 414a of the translation linkage arm 414. The translation linkage arm 414 may include a proximal housing portion 414b rigidly coupled or integrally formed with a distal arm portion 414c. The distal arm portion 414c may be curved or otherwise shaped to accommodate clearance of other components of the manipulator assembly 400 or the anatomy of the patient P. The follower 412 may be positioned in and constrained by the track 408 to move along a path defined by the track 408. In some embodiments the follower 412 may be translationally fixed to and rotatably coupled to the translation linkage arm 414 such that the follower 412 may turn as it moves along the track 408 to minimize frictional forces. The translation linkage arm 414 may also be translatably coupled to the pivot linkage arm 404 such that the translation linkage arm 414 may have a translational motion 407 in the XY plane relative to the pivot linkage arm 404. The translation linkage arm 414 may, for example, couple with and traverse a linear rail or linear groove feature of the pivot linkage arm 404 to allow linear movement 407 and restrict rotational motion. In other examples, the translation arm may telescope with the pivot linkage arm. As the translation linkage arm 414 is extended or retracted with the translation motion 407, the follower 412 within the track 408 may cause the pivot linkage arm 404 and the translation linkage arm 414 to pivot in unison with the rotation motion 405 as the follower 412 moves along the curvilinear shape of the track 408. In other words, a single motor or actuator may be used to actuate both the translational motion 407 and the rotational motion 405. A distal end 414d of the translation linkage arm 414 may be rotatably coupled to a distal linkage arm 416 (e.g., a fourth linkage arm) by a distal pivot joint 418 such that the distal linkage arm 416 moves with a rotation motion 409 about the pivot joint 418 in the XY plane. The distal linkage arm 416 may include or be coupled to an instrument holder configured to support and articulate a detachable instrument 421 (e.g., instrument 104). The instrument holder may include a carriage 415 configured for mounting the instrument to the manipulator assembly 400. The carriage 415 may be slidingly associated with the distal linkage arm 416 to translate the instrument with respect to the distal linkage arm 416. The carriage 415 may also include one or more motors or actuators for actuating components of the instrument (e.g., articulation and/or manipulation of an end effector of the instrument). A cannula 420 may be removably coupled to a distal end 416a of the distal linkage arm 416 by a clamp 422. The cannula 420 may be part of the instrument holder and may be spaced apart from the carriage as shown in FIG. 6. The cannula 420 may have an inner channel sized to receive a shaft of the instrument through the channel. As the linkage arms 402, 404, 414, and 416 are moved, the carriage 415, cannula 420 and mounted instrument 421 may be constrained to move in an XY plane about the remote center of motion RC fixed in the XY plane in the orientations in FIGS. 3-11. Thus, the instrument holder (e.g., the cannula 420 and the motor carriage 415) may be constrained in rotational motion to pivoting about the remote center of motion RC while the carriage 415 is further constrained to an insertion motion along an insertion axis along the distal linkage arm 416. The distal end 414d of the translation linkage arm 414 may trace an arc 423 (FIG. 10) around the remote center of motion RC. Consequently, the instrument 421 mounted to the distal linkage arm 416 via the carriage and inserted into the cannula 420 may pivot about a pitch axis 419 extending through the remote center of motion RC and may also pivot about the yaw axis 417 extending through the remote center of motion RC. The pitch axis 419 may be perpendicular to the yaw axis 417. The term "pitch" is arbitrary, and under this term it can be seen that with the remote center of motion RC stationary, rotation around the pitch axis 419 will cause the distal tip of the surgical instrument 421 to move in a way defined as pitch.

With reference to FIG. 2 and FIG. 6, in some embodiments, the distal linkage arm 316, 416 may be mounted such that the instrument holder including the carriage 315, 415 and/or the cannula 320, 420 are oriented toward or face a proximal direction (such as, for example, in the positive X direction of FIG. 6). Thereby, the instrument holder including the carriage 315, 415 and/or the cannula 320, 420 may face a direction proximal to the distal linkage arm 316, 416 and toward proximal components of the manipulator assemblies 300, 400. In other embodiments, the distal linkage arm 316, 416 may be mounted such that the instrument holder including the carriage 315, 415 and/or the cannula 320, 420 are oriented toward or face a distal direction (such as, for example, in the negative X direction of FIG. 2). Thereby, the instrument holder including the carriage 315, 415 and/or the cannula 320, 420 may face a direction distal to the manipulator assemblies 300, 400.

The translational motion 407 of the translation linkage arm 414 with respect to the pivot linkage arm 404 may be driven by an actuation mechanism 424 including an actuator 424a such as an electric motor, a hydraulic actuator, or a pneumatic actuator. The actuation mechanism 424 may be housed inside the housing 404a of the pivot linkage arm 404. The actuation mechanism 424 may also include a gear assembly or other mechanical assembly (not shown) to control the direction and speed of the output of the actuator 424a. The actuation mechanism 424 may be controlled by a control system (e.g., control system 110). Because the rotational motion 405 and the translational motion 407 are coupled as described above, the actuation mechanism 424 may cause both the rotational motion 405 and the translational motion 407 to be moved by a single motor or actuator. The translational motion 407 may be driven by a motor or actuator of the actuation mechanism 424, and the rotational motion 405 may also be pivoted as a function of the translational motion 407 (e.g., the amount of rotational motion 405 may be a function of the amount of driven translational motion 407). Thereby, a separate motor or actuator would not be required to drive the rotational motion 405. In this embodiment, the actuator 424a may be coupled to a linear motion mechanism 425. The linear motion mechanism 425 may be a drive screw, such as a lead screw or a ball screw having a threaded shaft 424b coupled to a threaded nut 424c. The threaded shaft 424b may be fixed within the housing 404a of the pivot linkage 404. The threaded nut 424c may be coupled to the follower 412. A gear assembly or other mechanical assembly of the actuation mechanism 424 may couple the threaded nut 424c to the output of the actuator 424a to advance or retract the follower 412 along the track 408. As the threaded nut 424c is driven along the threaded shaft 424b, the follower 412 (coupled to the threaded nut 424c) is driven along the track 408. In alternative embodiments, an actuation mechanism may drive rotational motion of the threaded shaft 424b to cause the threaded nut 424c to move along the threaded shaft 424b. Because of the curvilinear shape of the track 408, movement of the threaded nut 424c along the threaded shaft 424b may cause the pivot linkage arm 404 and the coupled translation linkage arm 414 to pitch or pivot 405 about the proximal pivot joint 406. Concurrently with the pivot motion 405, the movement of the threaded nut 424c along the threaded shaft 424b may cause the translation linkage arm 414 to extend or retract (translation motion 407) with respect to the pivot linkage arm 404. In some embodiments, the coupling of the translation motion 407 and rotation motion 405 may provide a functional relationship between the two motions. Because a single actuator 424a drives both the translation motion 407 and the rotation motion 405 and because the actuator 424a is positioned in a proximal portion of the manipulator assembly 400, the size and weight of the linkage arms may be minimized because they do not support the weight of a separate actuator to drive each motion.

The rotational motion 409 of the distal linkage arm 416 with respect to the translation linkage arm 414 may be driven by an actuation mechanism 426. In some embodiments, the actuation mechanism 426 may include an actuator 426a such as an electric motor, a hydraulic actuator, or a pneumatic actuator housed within the proximal housing portion 414b of the translation linkage arm 414. The actuation mechanism 426 may also include a gear assembly or other mechanical assembly (not shown) to control the direction and speed of the output of the actuator 426a. In this embodiment, the distal pivot motion 409, driven by a dedicated actuator 426a, may be controlled independently of the proximal pivot/translational motion 405/407. The actuation mechanism 426 may be controlled by the control system (e.g., control system 110). In this embodiment, the actuation mechanism 426 may be coupled to the distal linkage arm 416 by a distal pivot motion mechanism 428 that includes a linear motion mechanism such as a ball screw including an elongated threaded shaft 428a coupled to a threaded nut 428b. An auxiliary linkage arm 428c (e.g., a fifth linkage arm) is rotatably coupled at a proximal end to the threaded nut 428b and at a distal end to the distal linkage arm 416 at a distal joint 430. In this embodiment, the distal joint 430 may be spaced apart from the distal pivot joint 418.

In various alternative embodiments, separate actuators may drive translation motion 407, rotation motion 405, and rotational motion 409. In various alternative embodiments, a single actuation mechanism may drive coupled motion of the system joints. For example, a single actuation mechanism may drive rotational motion 405, translational motion 407, and distal pivot motion 409. In various alternative embodiments, the actuation mechanism 426 may drive coupled motion of the translational motion 407 and distal pivot motion 409, while the actuation mechanism 424 drives only the rotational motion 305.

Figure 7:
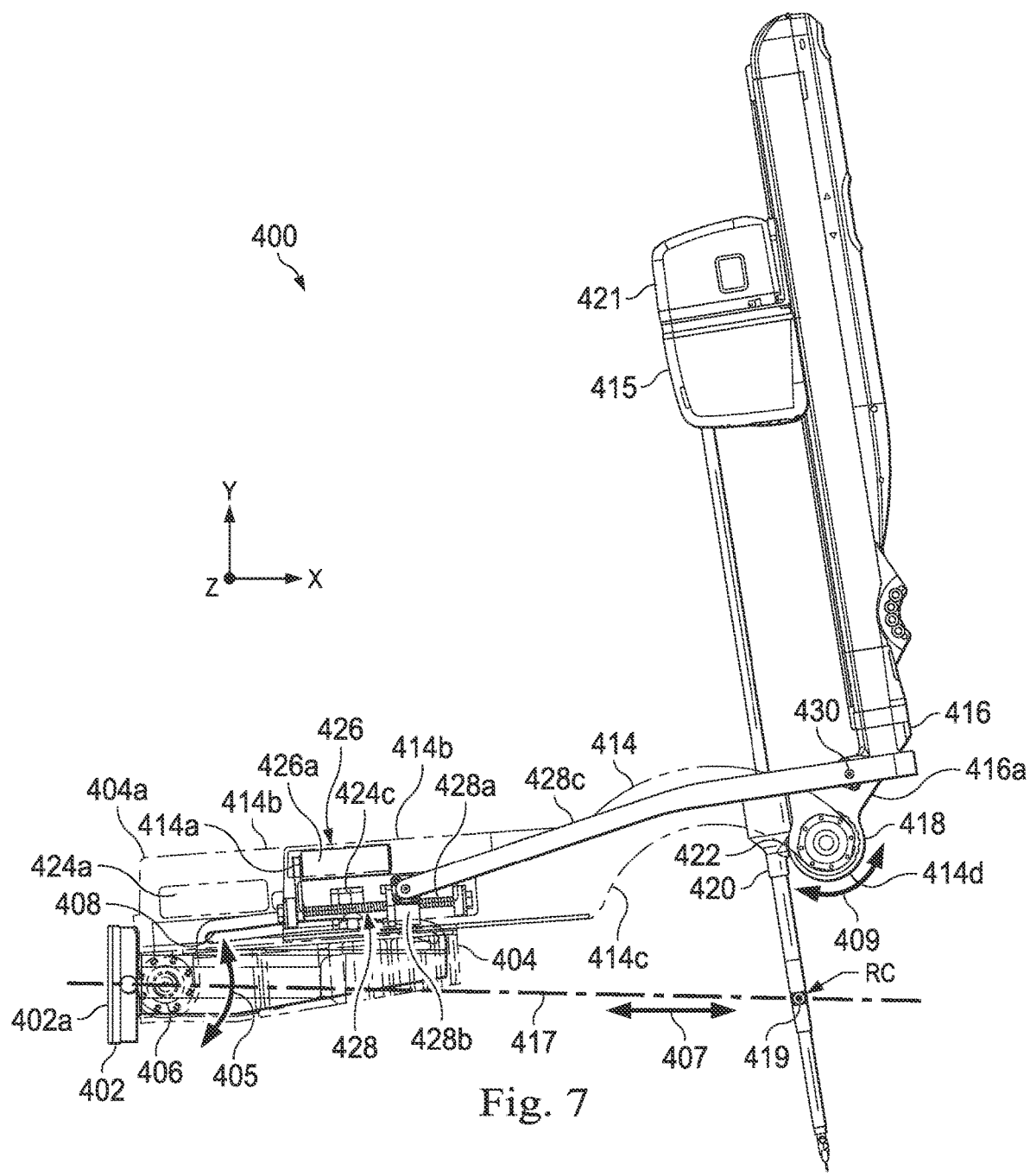
FIG. 7 is an opposite side view of the manipulator assembly in the partially extended or mid-extension configuration of FIG. 6 according to some embodiments.
Figure 8:
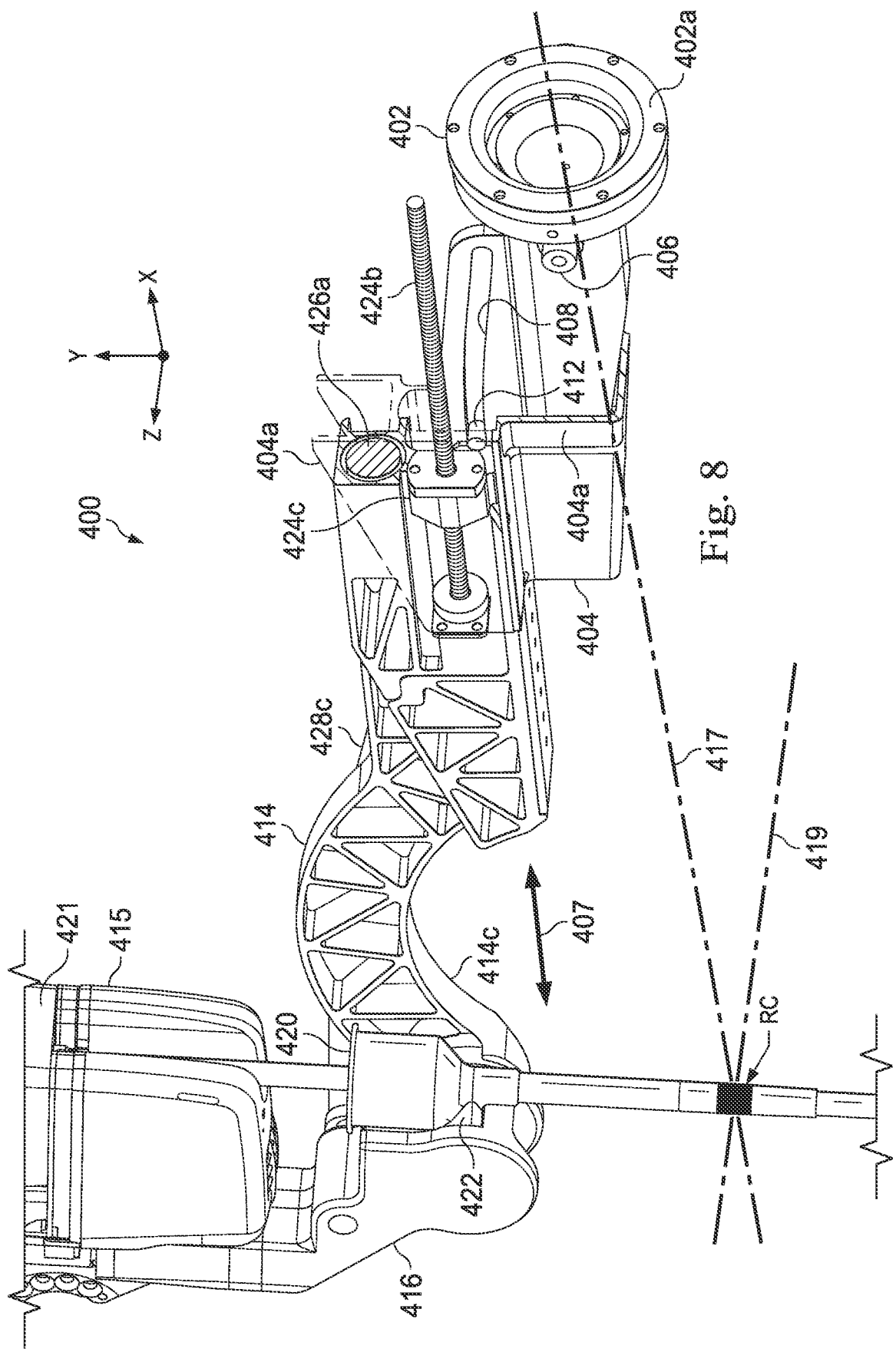
FIG. 8 is a perspective view of a portion of the manipulator assembly in the partially extended or mid-extension configuration of FIG. 6, according to some embodiments.
Figure 9:
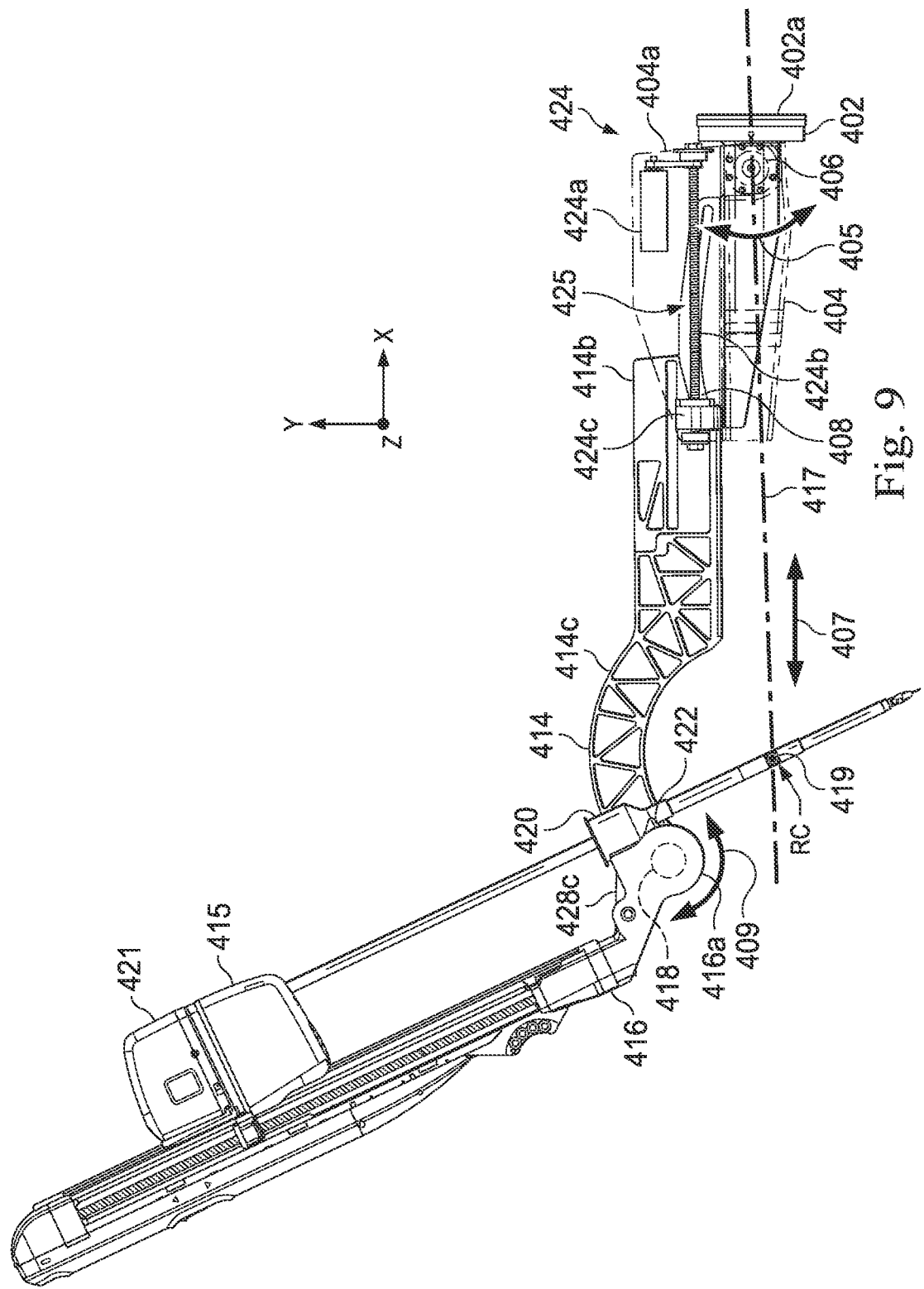
FIG. 9 is a side view of the manipulator assembly of FIG. 3 in an extended configuration according to some embodiments.
Figure 10:
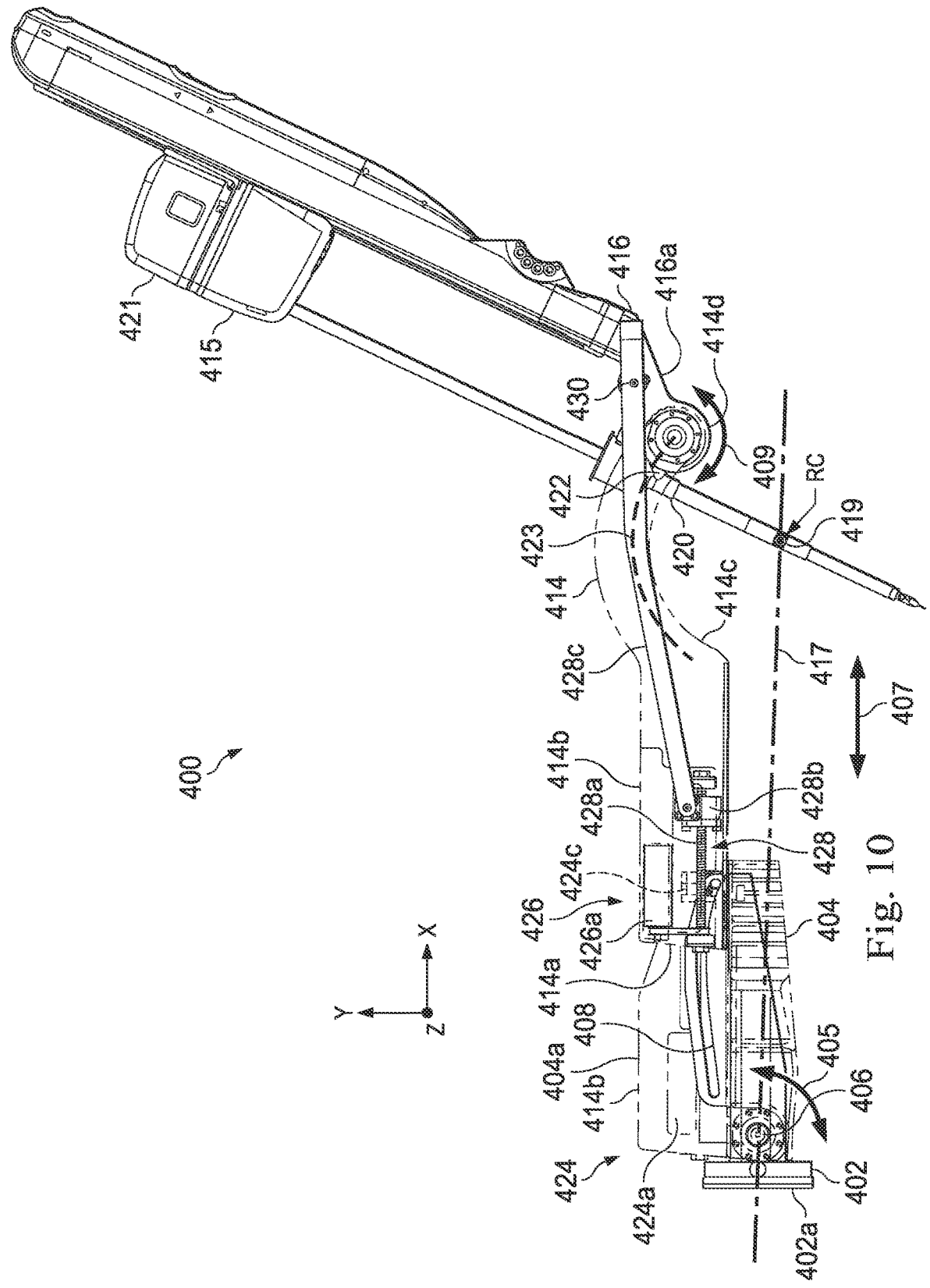
FIG. 10 is an opposite side view of the manipulator assembly in the extended configuration of FIG. 9 according to some embodiments.
Figure 11:
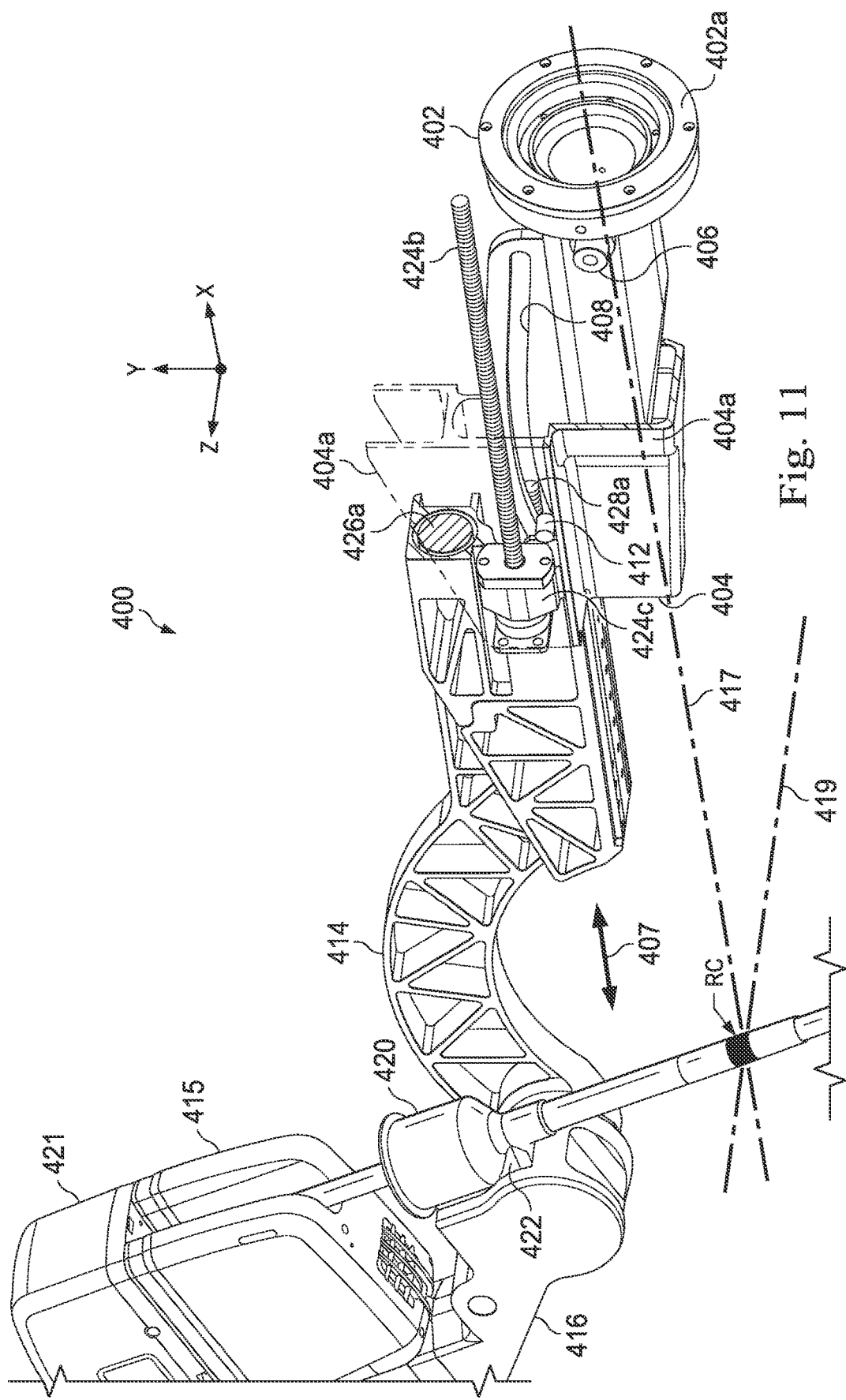
FIG. 11 is a perspective view of a portion of the manipulator assembly in the extended configuration of FIG. 9, according to some embodiments.

FIGS. 6-8 illustrate the manipulator assembly 400 in a partially extended or mid-extension configuration. FIG. 6 provides a side view of the manipulator assembly 400, and FIG. 7 provides the opposite side view of the manipulator assembly. FIG. 8 provides a perspective, cut-away view a portion of the manipulator assembly 400 in the partially extended or mid-extension configuration. FIGS. 9-11 illustrate the manipulator assembly 400 in an extended configuration. FIG. 9 provides a side view of the manipulator assembly 400, and FIG. 10 provides the opposite side view of the manipulator assembly. FIG. 11 provides a perspective, cut-away view a portion of the manipulator assembly 400 in the extended configuration.

Figure 12:
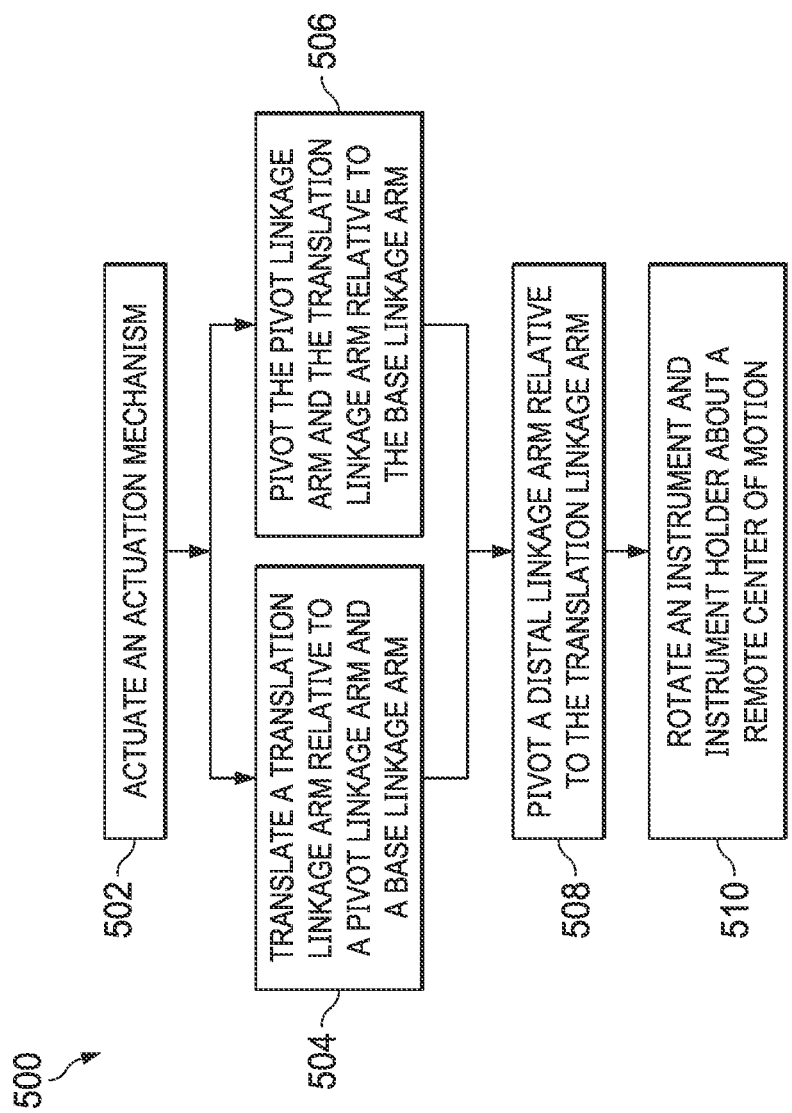
FIG. 12 illustrates a method for operating a manipulator transmission system according to some embodiments.

FIG. 12 illustrates a method 500 for operating the manipulator assembly 400 according to some embodiments. The method 500 is illustrated as a set of operations or processes 502 through 510 and is described with continuing reference to FIGS. 3-11. Not all of the illustrated processes may be performed in all embodiments of method 500. Additionally, one or more processes that are not expressly illustrated in FIG. 12 may be included before, after, in between, or as part of the processes 502 through 510. In some embodiments, one or more of the processes may be implemented, at least in part, in the form of executable code stored on non-transitory, tangible, machine-readable media that when run by one or more processors (e.g., the processors of a control system) may cause the one or more processors to perform one or more of the processes. In one or more embodiments, the processes may be performed by the control system 110.

At a process 502, the actuation mechanism 424 may be actuated to drive the follower 412 along the track 408. More specifically, the actuator 424a may drive the threaded nut 424c that is coupled to the follower 412 to advance or retract the follower 412 along the track 408. At a process 504, the translation linkage arm 414 translates with respect to the pivot linkage arm 404 and the base linkage arm 402. More specifically, the movement of the follower 412 along the track 408 may advance or retract the translation linkage arm relative to the pivot linkage arm 404 and the base linkage arm 402. The translation motion 407 of the translation linkage arm 414 is shown in the partially extended or mid-extension configuration of FIGS. 6-8. As shown in FIG. 7, translation motion 407 also translates the actuation mechanism 426 housed within the proximal housing portion 414b of the translation linkage arm 414. The translation motion 407 of the translation linkage arm 414 is also shown in the extended configuration of FIGS. 9-11. A fully extended configuration may be reached when the follower 412 reaches a distal-most end of the track 408 as shown in FIGS. 9 and 11.

Concurrently with the process 504, at a process 506, the pivot linkage arm 404 and the translation linkage arm 414 pivot relative to the base linkage arm 402. More specifically, the movement of the follower 412 along the track 408 may pivot the pivot linkage arm 404 and the coupled translation linkage arm 414 with respect to the base linkage arm 402. For example, when the follower 412 is in a proximal portion of the track 408, the pivot linkage arm 404 may pitch or pivot increasingly upward (+Y direction), and when the follower 412 is in a distal portion of the track 408, the pivot linkage arm 404 may pitch or pivot increasingly downward (−Y direction). As shown in the partially extended or mid-extension configuration of FIGS. 6 and 7, the housing 404a may pivot closer to or contact the proximal flange 402a as the follower 412 reaches an apex of the curvilinear shape and the pivot linkage arm 404 pivots about the proximal pivot joint 406.

At a process 508, that may be performed before, after, or concurrently with processes 504/506, the distal linkage arm 416 pivots relative to the translation linkage arm 414. More specifically, the actuator mechanism 426 may be actuated to advance or retract the threaded nut 428b along the threaded shaft 428a. As the threaded nut 428b is advanced or retracted, the auxiliary linkage arm 428c coupled to the threaded nut 428b is also advanced or retracted. The partial or mid-advancement of the auxiliary linkage arm 428c is shown in the partially extended or mid-extension configuration of FIG. 7. The translation motion of the auxiliary linkage arm 428c is also shown in the extended configuration of FIG. 10. A fully advanced position of the auxiliary linkage arm 428c may be reached when the threaded nut 428b reaches a distal-most end of the threaded shaft 428a as shown in FIG. 10. As the proximal end of the auxiliary linkage arm 428c is advanced by the threaded nut 428b, the distal end of the auxiliary linkage arm drives the distal linkage arm 416 to pivot about the distal joint 430, thereby forcing the distal linkage arm 416 to pivot about the distal pivot joint 418.

At a process 510, the instrument 421 rotates about the remote center of motion RC. More specifically, as the distal linkage arm 416 pivots about the distal pivot joint 418, the instrument 421, as well as the carriage and the cannula 420, which are attached to the distal linkage arm 416, each pivot about the remote center of motion RC. Optionally, the yaw joint may be driven via an actuation mechanism to rotate the base linkage arm 402 about the yaw axis 417 to cause yaw motion to the manipulator assembly 400, as described above. The yaw motion may occur before, after, or concurrently with any of the processes 502 through 510.

Figure 13:
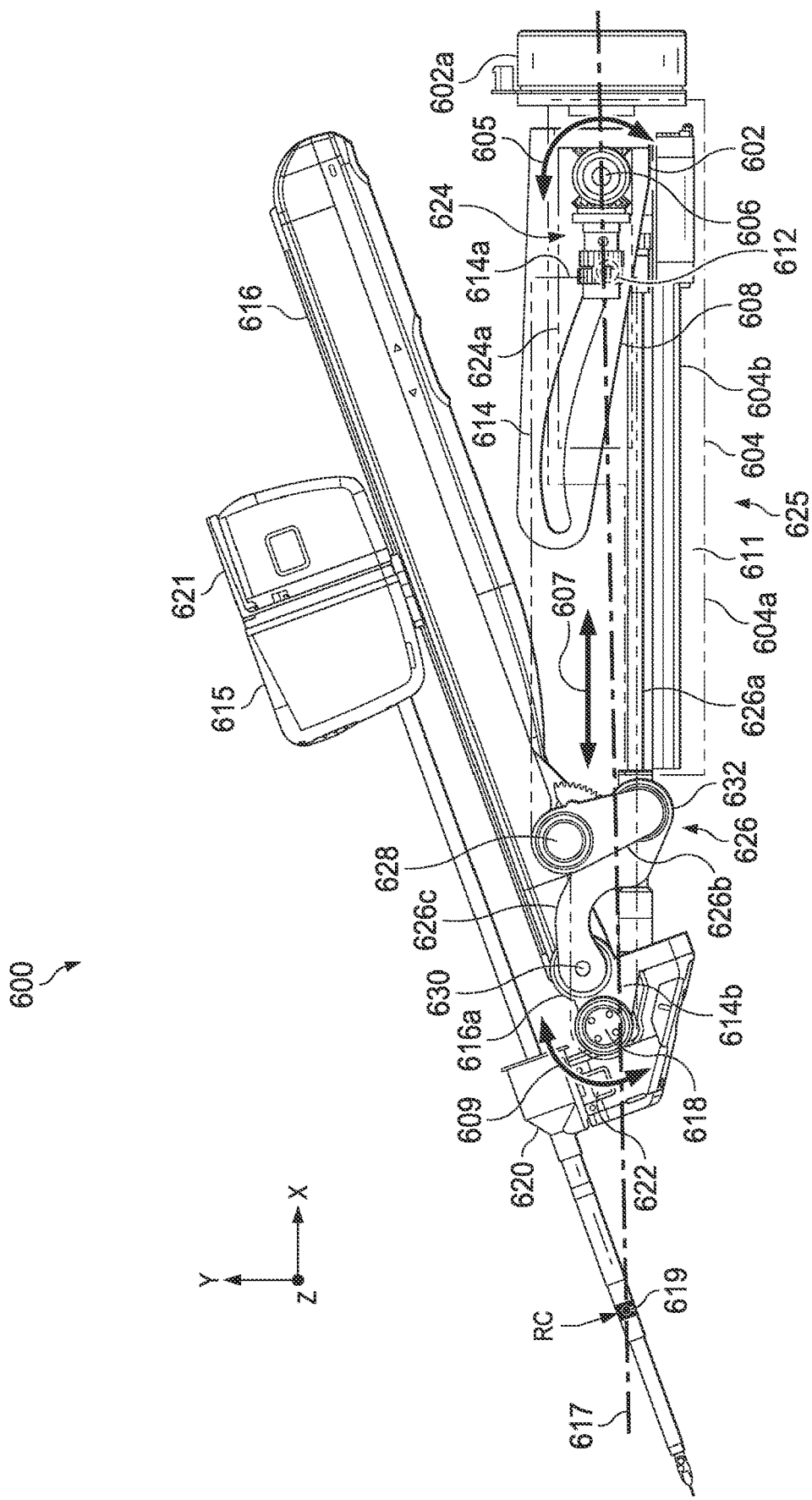
FIG. 13 is a side view of a manipulator assembly in a retracted configuration according to some embodiments.
Figure 14:
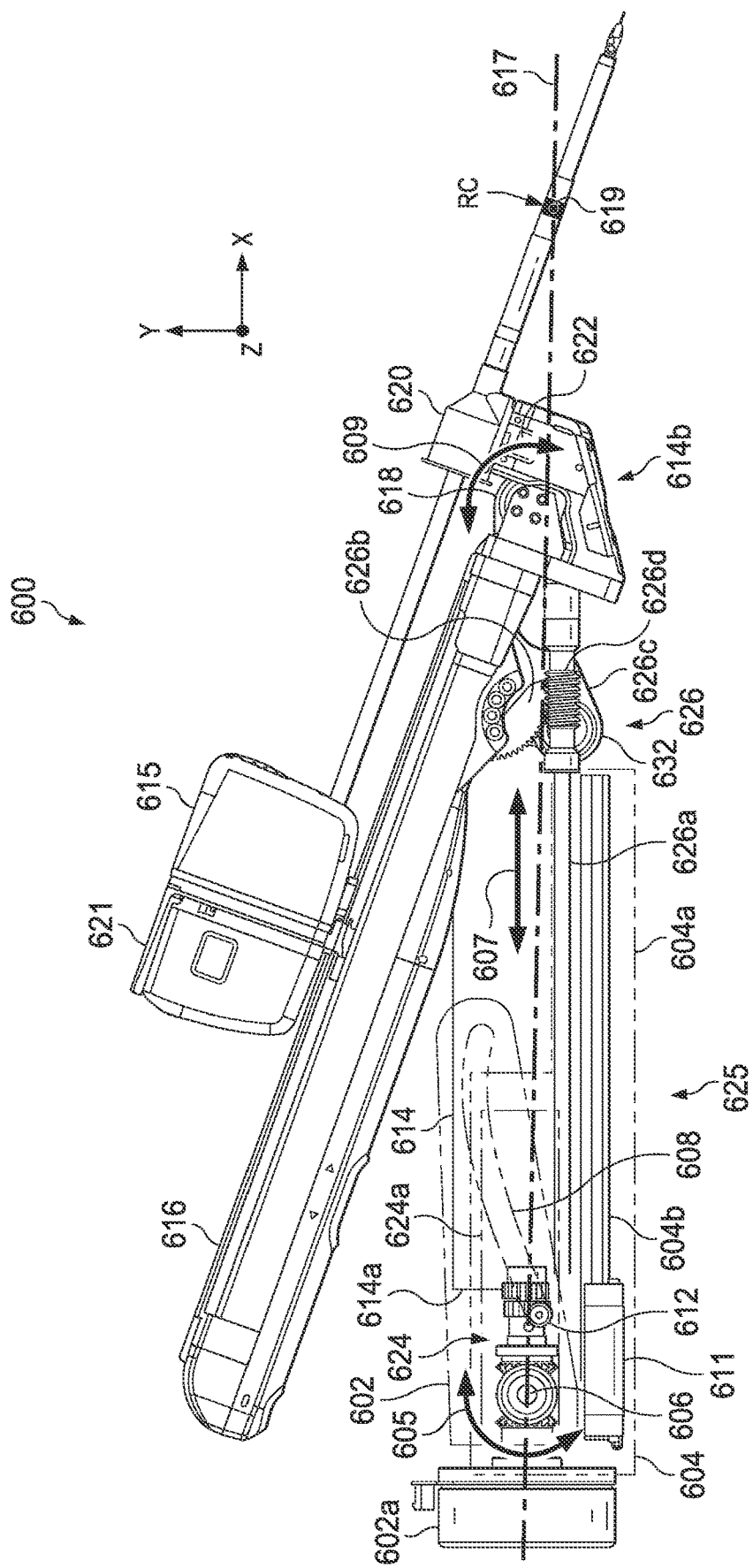
FIG. 14 is an opposite side view of the manipulator assembly of FIG. 13 in the retracted configuration according to some embodiments.

FIGS. 13-19 illustrate a manipulator assembly 600 in a manipulator frame of reference having a Cartesian coordinate system (X, Y, Z) according to some embodiments. The manipulator assembly 600 may be used as the manipulator assembly 102/202 described above. FIGS. 13 and 14 illustrate the manipulator assembly 600 in a retracted configuration. FIG. 13 provides a side view of the manipulator assembly 400, and FIG. 14 provides the opposite side view of the manipulator assembly. In this embodiment, a linkage assembly may include a base linkage arm 602 (e.g., a first linkage arm), a pivot linkage arm 604 (e.g., a second linkage arm), a translation linkage arm 614 (e.g., a third linkage arm), and a distal linkage arm 616 (e.g., a fourth linkage arm). The base linkage arm 602 may be coupled to the pivot linkage arm 604 by a proximal pivot joint 606 such that the pivot linkage arm 604 moves in a rotation motion 605 about the pivot joint 406 in the XY plane in the orientations shown in FIGS. 13-19. A proximal end of the base linkage arm 602 and a proximal end of the pivot linkage arm 604 may be coupled at the proximal pivot joint 406. The base linkage arm 602 may include a guide or track 608 (e.g., a cam race) that may have a curvilinear shape. The track may be, for example, a curvilinear slot. The pivot linkage arm 604 may include a housing 604a. In some embodiments, a proximal flange 602a of the base linkage arm 402 may be fixed to the table T or other structure held stationary during the medical procedure. In other embodiments, the base linkage arm 602 may be rotationally coupled to a more proximal linkage via a yaw joint. The yaw joint may rotationally couple a proximal end of the base linkage arm 602 (e.g., proximal flange 602a of the base linkage arm 402) to the distal end of the more proximal linkage. The yaw joint may be driven by an actuation mechanism, for example, an actuator such as an electric motor, a hydraulic actuator, or an pneumatic actuator and a gear assembly or other mechanical assembly to control the direction and speed of the output of the actuator. The yaw joint is operable to produce controlled rotation (roll) of the base linkage arm 602 about a yaw axis that intersects the remote center of motion RC, the rotation corresponding to motion about the YZ plane in the orientations in FIGS. 13-19. The rotation of the base linkage arm 602 about the yaw axis causes corresponding yaw motion of the portions of the manipulator assembly 600 distal to the base linkage arm 602, while maintaining the remote center of motion RC.

The translation linkage arm 614 may be coupled to the base linkage arm 602 by a follower 612 (e.g. cam follower) that is coupled to a proximal portion 614a of the translation linkage arm 614. The translation linkage arm 614 may include the proximal portion 614a rigidly coupled or integrally formed with a distal portion 614b. The follower 612 may be positioned in and may be constrained to move along a path defined by the track 608. In some embodiments, the follower 612 may be translationally fixed and rotatably coupled to the translation linkage arm 614 such that the follower 612 may turn as it moves along the track 608 to minimize frictional forces. The translation linkage arm 614 may also be translatably coupled to the pivot linkage arm 604 such that the translation linkage arm 614 may have a translational motion 607 in the XY plane relative to the pivot linkage arm 604. The translation linkage arm 614 may, for example, include or be rigidly coupled to a shuttle 611. The shuttle 611 may couple with and traverse a linear rail 604b or linear groove feature of the pivot linkage arm 604 to allow linear movement 607 of the translation linkage arm 614 and restrict rotational motion relative to the pivot linkage arm 604. As the translation linkage arm 614 is extended or retracted with the translation motion 607, the follower 612 within the track 608 may cause the pivot linkage arm 604 and the translation linkage arm 614 to pivot in unison with the rotation motion 605 as the follower 612 moves along the curvilinear shape of the track 608. The distal portion 614b of the translation linkage arm 614 may be rotatably coupled to the distal linkage arm 616 by a distal pivot joint 618 such that the distal linkage arm 616 moves with a rotation motion 609 about the pivot joint 618 in the XY plane. The distal linkage arm 616 may include or be coupled to an to an instrument holder configured to support and articulate a detachable instrument. The instrument holder may include a carriage 615 configured for mounting the instrument to the manipulator assembly 600. The carriage 615 may be slidingly associated with the distal linkage arm 616 to translate the instrument with respect to the distal linkage arm 616. The carriage 615 may also include one or more motors or actuators for actuating components of the instrument (e.g., articulation and/or manipulation of an end effector of the instrument). A cannula 620 may be removably coupled to a distal end 616a of the distal linkage arm 416 by a clamp 622. The cannula 620 may be part of the instrument holder, and may be spaced apart from the carriage. The cannula 620 may have an inner channel sized to receive a shaft of the instrument through the channel. As the linkage arms 602, 604, 614, and 616 are moved, the carriage 615, cannula 620, and mounted instrument 621 cannula 620 may be constrained to move about a remote center of motion RC that is substantially fixed in the XY plane in the orientations in FIGS. 13-19. Thus, the instrument holder (e.g., the cannula 620 and the motor carriage 615) may be constrained in rotational motion to pivoting about the remote center of motion RC while the carriage 615 is further constrained to an insertion motion along an insertion axis along the distal linkage arm 616. Consequently, an instrument 621 mounted to the distal linkage arm 616 via the carriage and inserted into the cannula 620 may pivot about a pitch axis extending through the remote center of motion RC and may also pivot about the yaw axis extending through the remote center of motion RC.

The translational motion 607 of the translation linkage arm 614 with respect to the pivot linkage arm 604 may be driven by an actuation mechanism 624 including an actuator 624a such as an electric motor, a hydraulic actuator, or a pneumatic actuator. The actuation mechanism 624 may be housed inside the housing 604a of the pivot linkage arm 604. The actuation mechanism 624 may also include a gear assembly or other mechanical assembly (not shown) to control the direction and speed of the output of the actuator 624a. The actuation mechanism 624 may be controlled by a control system (e.g., control system 110). Because the rotational motion 605 and the translational motion 607 are coupled, the actuation mechanism 624 may cause both the rotational motion 605 and the translational motion 607 to be moved by a single motor or actuator. The translational motion 607 may be driven by a motor or actuator of the actuation mechanism 624, and the rotational motion 605 may also be pivoted as a function of the translational motion 607 (e.g., the amount of rotational motion 605 may be a function of the amount of driven translational motion 607). Thereby, a separate motor or actuator would not be required to drive the rotational motion 605. In this embodiment, the actuator 624a may be coupled to a linear motion mechanism 625 including the shuttle 611 and the rail 604b. In alternative embodiments, the linear motion mechanism may include a ball screw configuration, similar to that described above for manipulator assembly 400 (see FIG. 3). A gear assembly or other mechanical assembly of the actuation mechanism 624 may couple the output of the actuator 424a to the linear motion mechanism 625 to advance or retract the follower 612 (which is fixedly coupled relative to the translation linkage arm 614 and the shuttle 611) along the track 608. As the shuttle 611 is driven along the rail 604b, the follower 612 is driven along the track 608. Because of the curvilinear shape of the track 608, movement of the shuttle 611 along the rail 604b may cause the pivot linkage arm 604 and the coupled translation linkage arm 614 to pitch or pivot 605 about the proximal pivot joint 606. Concurrently with the pivot motion 605, the movement of the shuttle 611 along the rail 604b may cause the translation linkage arm 614 to extend or retract (translation motion 607) with respect to the pivot linkage arm 604. The coupling of the translation motion 607 and rotation motion 605 provides a functional relationship between the two motions. Because a single actuator 624a drives both the translation motion 607 and the rotation motion 605 and because the actuator 624a is positioned in a proximal portion of the manipulator assembly 600, the size and weight of the linkage arms may be minimized because they do not support the weight of a separate actuator for each motion.

The rotational motion 609 of the distal linkage arm 616 with respect to the translation linkage arm 614 may be driven by a distal pivot motion mechanism 626. In some embodiments, the distal pivot motion mechanism 626 may include a link assembly, including a gear shaft 626a, an input link 626b and a coupler link 626c, that is coupled to the actuator 624a of the actuation mechanism 624 such that a single actuator controls the proximal pivot motion 605, the translation motion 607 and the distal pivot motion 609. In alternative embodiments, separate actuators may drive translation motion 607, rotation motion 605, and rotational motion 609. In various alternative embodiments, a single actuation mechanism may drive coupled motion of the system joints. For example, a single actuation mechanism may drive rotational motion 605, translational motion 607, and distal pivot motion 609. In various alternative embodiments, the actuation mechanism 626 may drive coupled motion of the translational motion 607 and rotational motion 609, while the actuation mechanism 624 drives only the rotational motion 605.

In this embodiment, the distal pivot motion 609 is driven by the distal pivot motion mechanism 626. The distal pivot motion mechanism 626 includes the gear shaft 626a which is coupled at a proximal end to the actuator 624a of the actuation mechanism 624, for example by a gear assembly (not shown). The gear shaft 626a may have a variable length (e.g. a telescoping length) to allow a proximal end of the gear shaft 626a to remain coupled to the actuation mechanism 624 while a distal end of the gear shaft 626a translates with the translation linkage arm 614. A distal end of the gear shaft 626a includes a worm gear 626d that engages the input link 626b. The input link 626b may have teeth sized and shaped to engage the worm gear 626d. In some embodiments, the input link 626b may be a crank that many rotate a full 360 degrees, a rocker that may rotate through a limited range of angles between 0 and 180 degrees, a 0-rocker that can rotate through a limited range of angles that include 0 degrees but not 180 degrees, or a it-rocker that can rotate through a limited range of angles that include 180 degrees but not 0 degrees. The input link 626b may be pivotally coupled at one end to the translation linkage arm 614 by a joint 628 and may be pivotally coupled at the opposite end to the coupler link 626c by a joint 632. The coupler link 626c may be coupled at an end opposite the joint 632 to the distal linkage arm 616 by a joint 630. In this embodiment, the pivot joint 630 may be spaced apart from the distal pivot joint 618. The coupler link 626c may include a recessed portion 633 sized and shaped to receive and extend around the distal pivot joint 618 when the manipulator assembly 600 is in an extended configuration.

Figure 15:
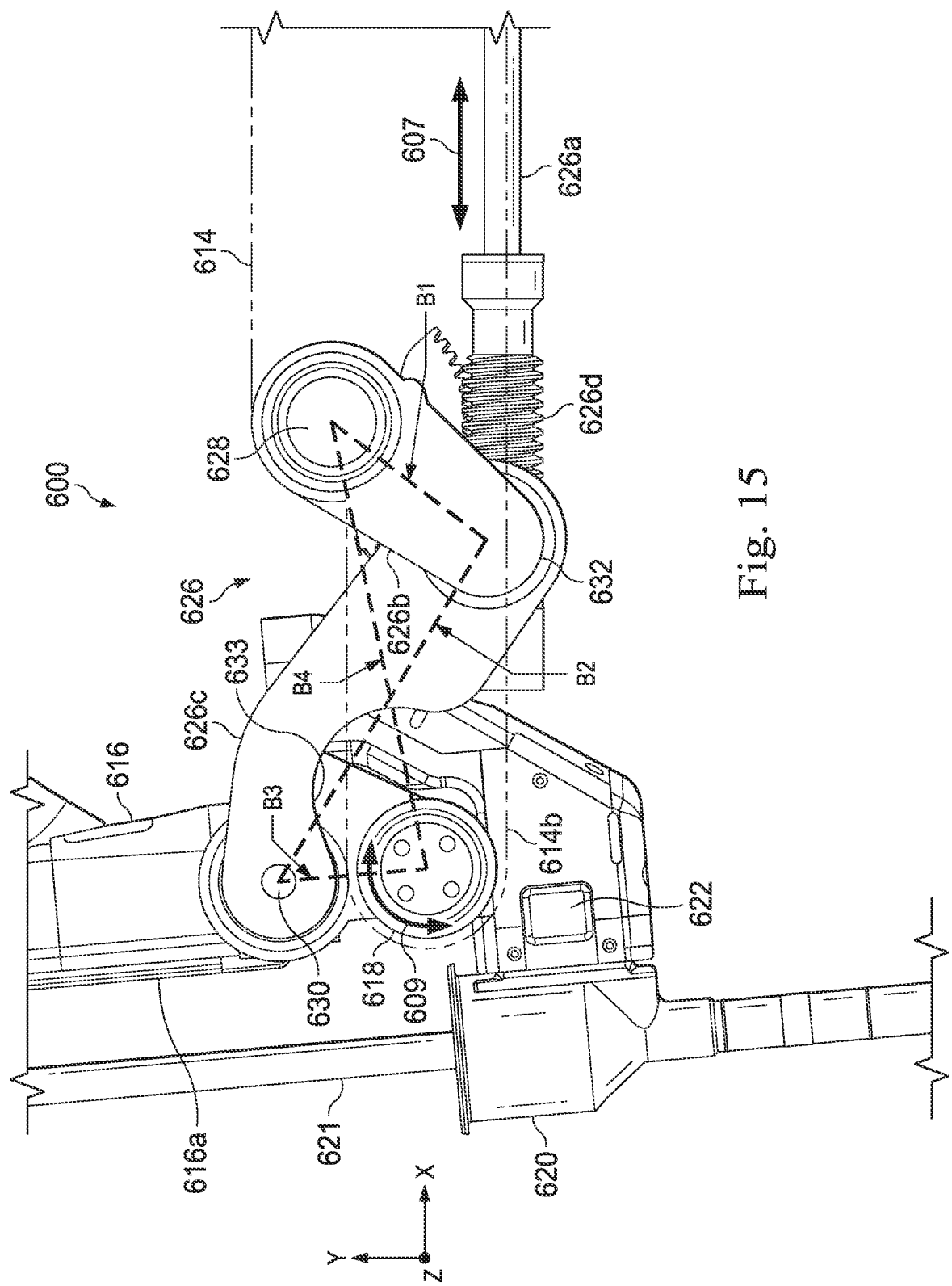
FIG. 15 is a side view of a portion of the manipulator assembly of FIG. 13 in a partially extended or mid-extension configuration according to some embodiments.
Figure 16:
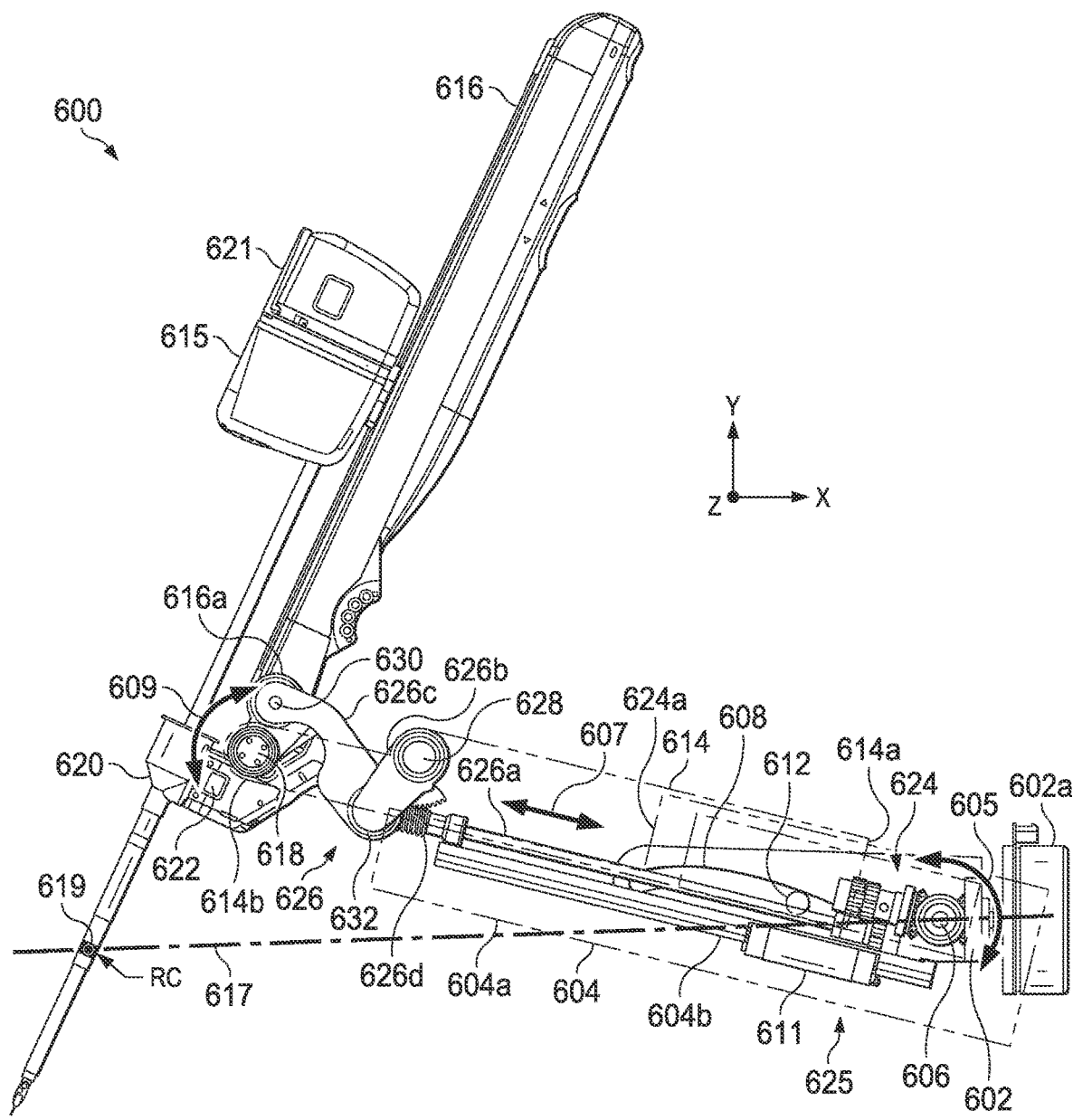
FIG. 16 is a side view of the manipulator assembly of FIG. 13 in a partially extended or mid-extension configuration according to some embodiments.
Figure 17:
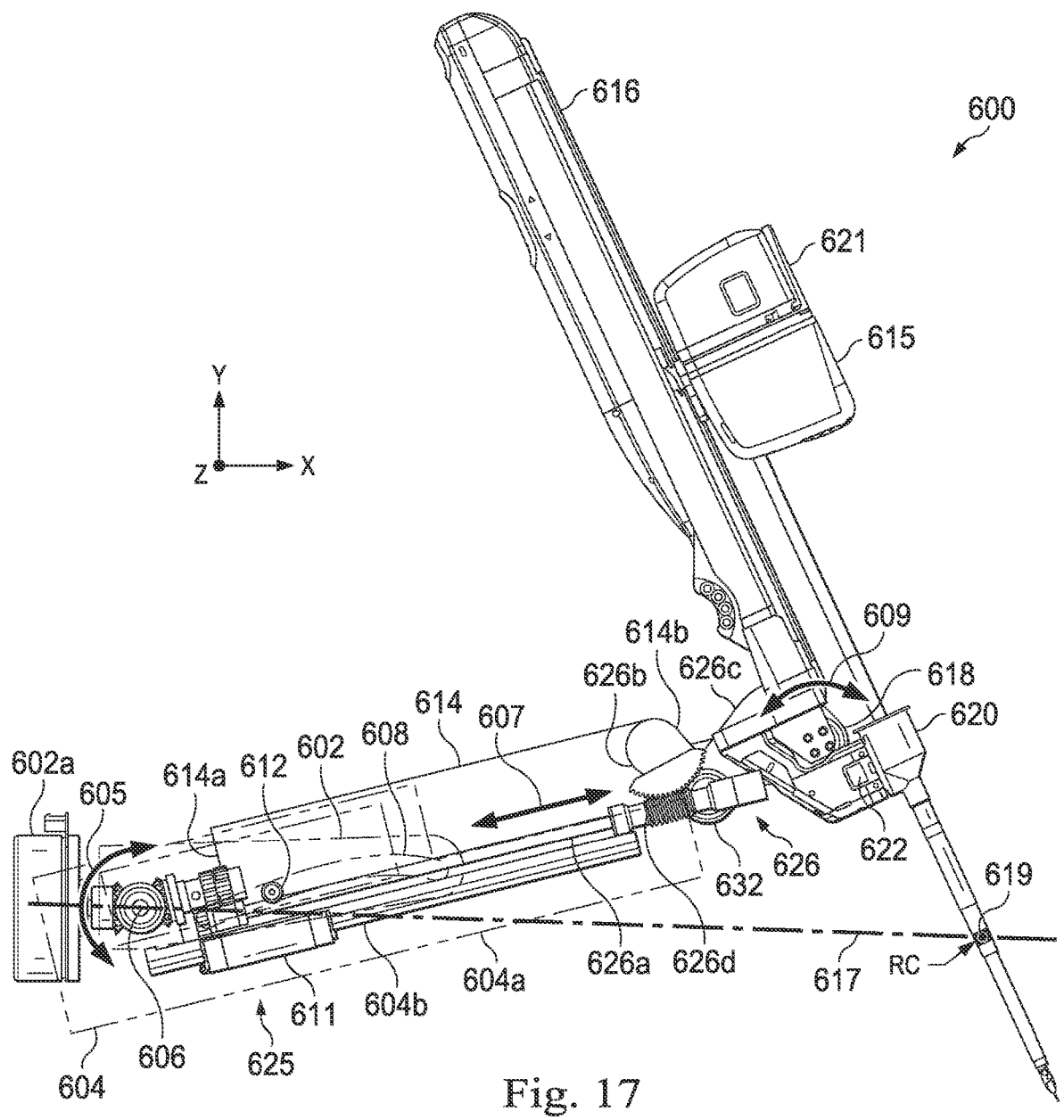
FIG. 17 is an opposite side view of the manipulator assembly in the partially extended or mid-extension configuration of FIG. 16 according to some embodiments.
Figure 18:
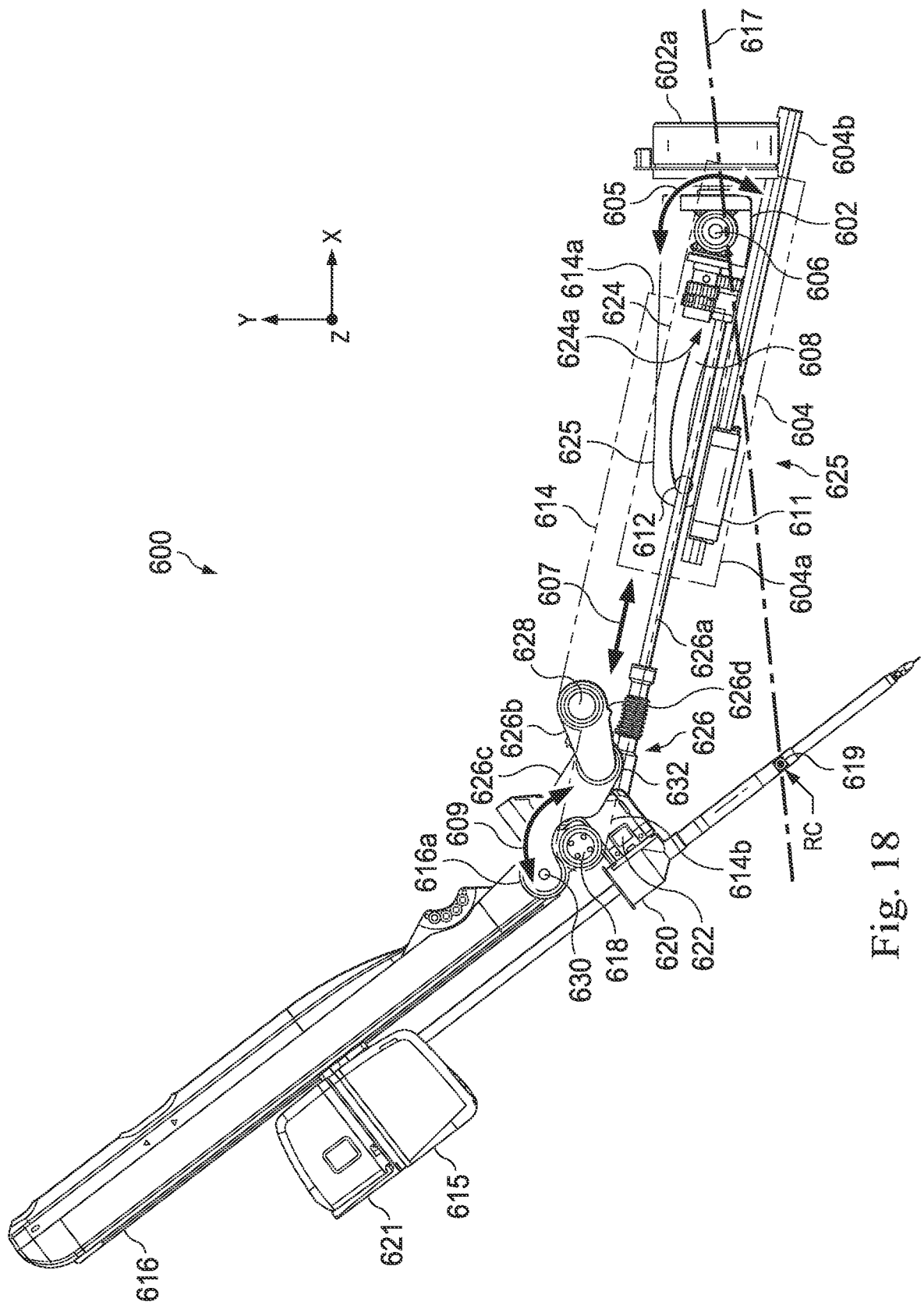
FIG. 18 is a side view of the manipulator assembly of FIG. 13 in an extended configuration according to some embodiments.
Figure 19:
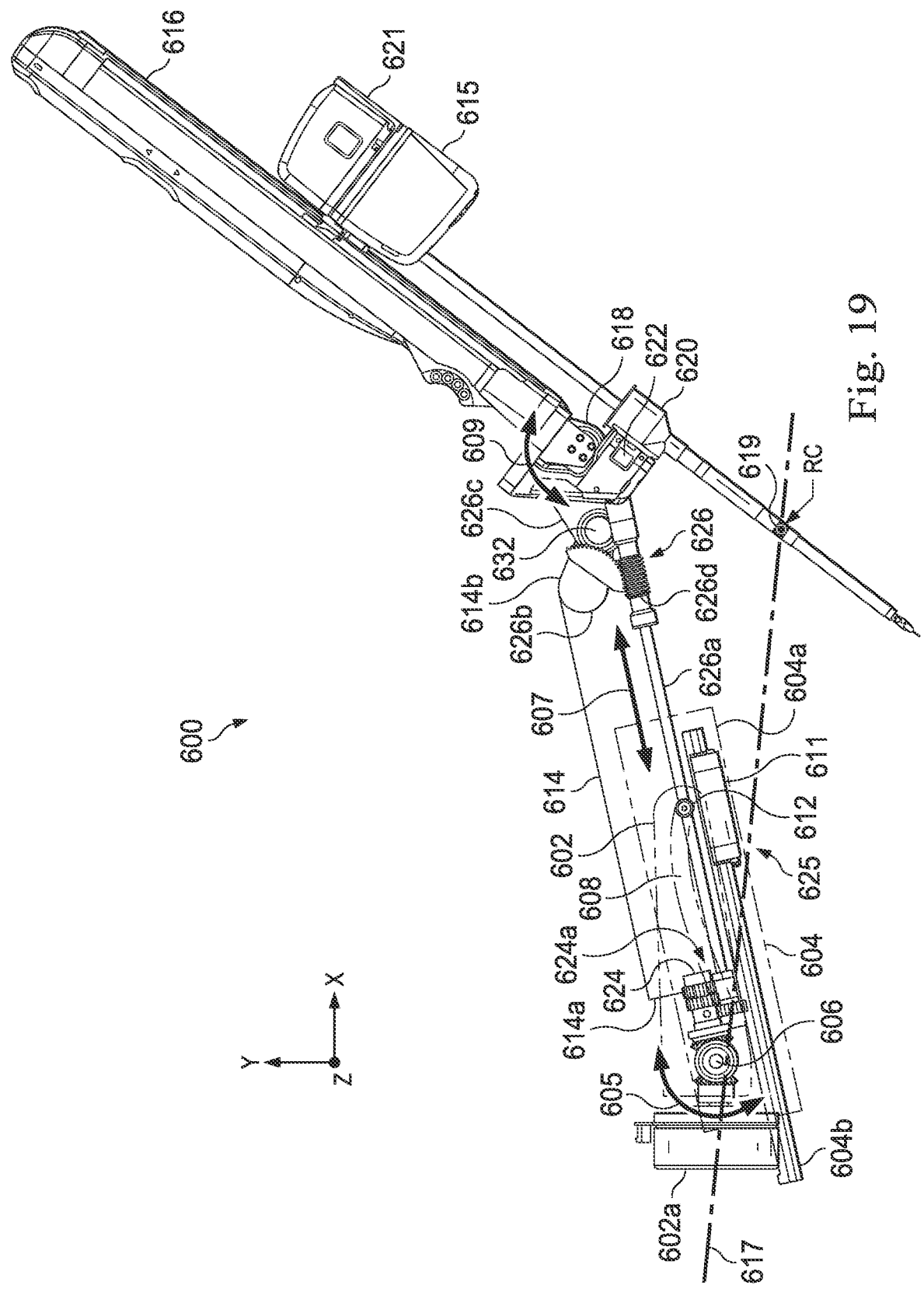
FIG. 19 is an opposite side view of the manipulator assembly in the extended configuration of FIG. 18 according to some embodiments.

FIG. 15 illustrates a more detailed view of the distal pivot motion mechanism 626 with the manipulator assembly in a partially extended or mid-extension configuration. FIGS. 16-17 illustrate the manipulator assembly 600 in a partially extended or mid-extension configuration. FIG. 16 provides a side view of the manipulator assembly 600, and FIG. 17 provides the opposite side view of the manipulator assembly. FIGS. 18-19 illustrate the manipulator assembly 600 in an extended configuration. FIG. 18 provides a side view of the manipulator assembly 600, and FIG. 19 provides the opposite side view of the manipulator assembly.

Figure 20:
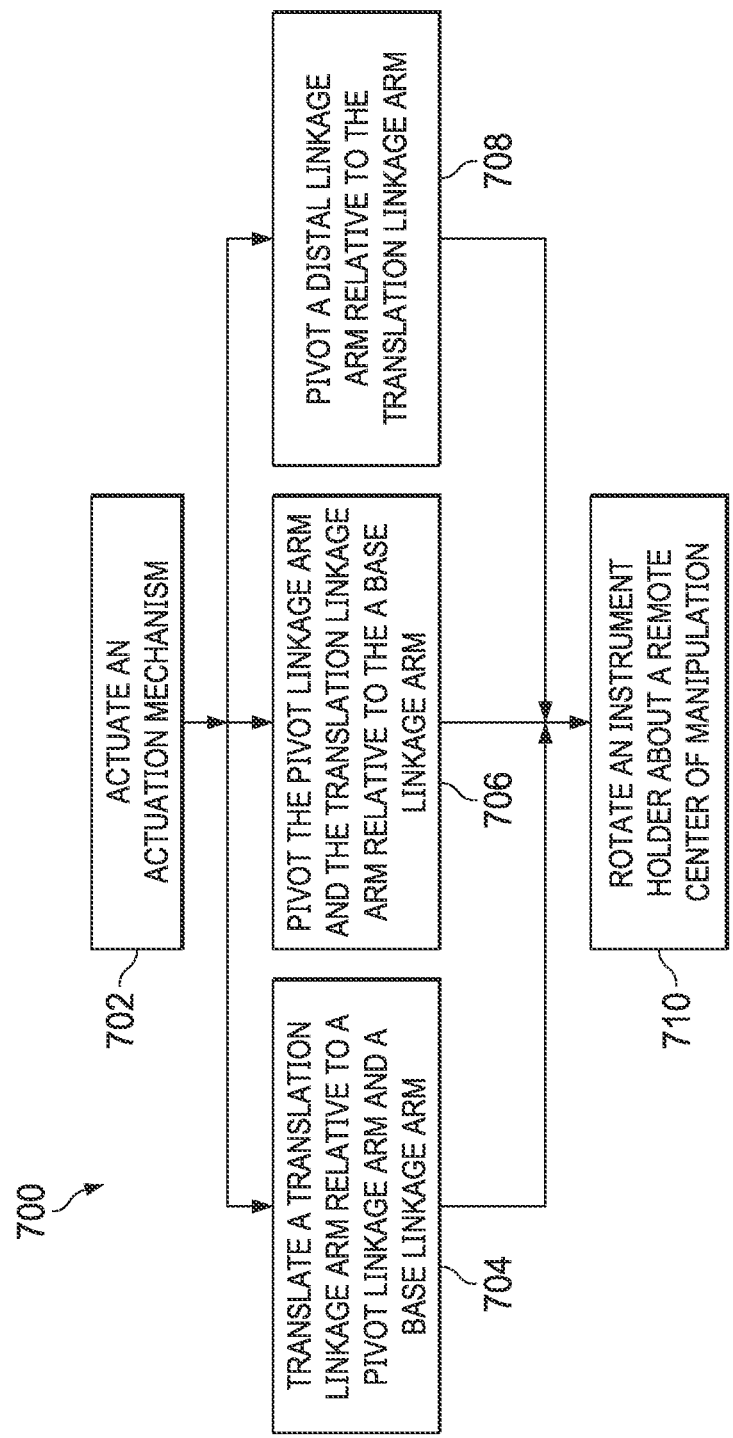
FIG. 20 illustrates a method for operating a manipulator transmission system according to some embodiments.

FIG. 20 illustrates a method 700 for operating the manipulator assembly 600 according to some embodiments. The method 700 is illustrated as a set of operations or processes 702 through 710 and is described with continuing reference to FIGS. 13-19. Not all of the illustrated processes may be performed in all embodiments of method 700. Additionally, one or more processes that are not expressly illustrated in FIG. 20 may be included before, after, in between, or as part of the processes 702 through 710. In some embodiments, one or more of the processes may be implemented, at least in part, in the form of executable code stored on non-transitory, tangible, machine-readable media that when run by one or more processors (e.g., the processors of a control system) may cause the one or more processors to perform one or more of the processes. In one or more embodiments, the processes may be performed by the control system 110.

At a process 702, the actuation mechanism 624 may be actuated to drive the follower 612 along the track 608. More specifically, the actuator 624a may drive the follower 612 to advance or retract the follower 612 along the track 608. At a process 704, the translation linkage arm 614 may translate with respect to the pivot linkage arm 604 and the base linkage arm 602. More specifically, the movement of the follower 612 along the track 608 may advance or retract the translation linkage arm 614 relative to the pivot linkage arm 604 and the base linkage arm 602. The translation motion 607 of the translation linkage arm 614 is shown in the partially extended or mid-extension configuration of FIGS. 16-17. The translation motion 607 of the translation linkage arm 614 is also shown in the extended configuration of FIGS. 18-19. A fully extended configuration may be reached when the follower 612 reaches a distal-most end of the track 608 as shown in FIG. 18.

Concurrently with the process 704, at a process 706, the pivot linkage arm 604 and the translation linkage arm 614 pivot relative to the base linkage arm 602. More specifically, the movement of the follower 612 along the track 608 may pivot the pivot linkage arm 604 and the coupled translation linkage arm 614 with respect to the base linkage arm 602. For example, when the follower 612 is in a proximal portion of the track 608, the pivot linkage arm 604 may pitch or pivot increasingly upward (+Y direction), and when the follower 612 is in a distal portion of the track 608, the pivot linkage arm 604 may pitch or pivot increasingly downward (−Y direction).

Concurrently with the process 704 and 706, at a process 708, the distal linkage arm 616 pivots relative to the translation linkage arm 614. In this embodiment, the actuation mechanism 624 may drive the motion of the distal pivot motion mechanism 626 to cause the rotational motion 609, and thus a common actuator 624a may drive the proximal pivot motion 605, the translation motion 607 and the distal rotational motion 609. Gearing assemblies may be used to provide different rotational output speeds to drive the distal and proximal motions. More specifically, the actuator 624a may drive one or more gears of the actuation mechanism 624 to turn the gear shaft 626a. Rotation of the gear shaft 626a turns the worm gear 626d. The worm gear 626d is engaged with the teeth of input link 626b, and as the worm gear 626d turns, the input link 626b pivots about the joint 628 causing the joint 632 to rotate about the joint 628. As the joint 628 rotates about the joint 628, the coupler link 626c (coupled to the input link 626b by the joint 632) translates relative to the worm gear 626d. As the manipulator assembly 600 moves into the fully extended configuration of FIGS. 18-19, the distal pivot joint 618 becomes nested in the recessed portion 629 of the coupler link 626c. The translation of the coupler joint 626c also causes the distal joint 630 to translate relative to the worm gear 626d and the coupler link 626c to pivot about the distal joint 630 relative to the distal linkage arm 616. Thus, the coupler link 626c drives the distal linkage arm 616 to pivot about the distal pivot joint 618.

As shown in FIG. 15, the distal pivot motion mechanism 626 may be considered a four-bar mechanism that is used to couple the rotation motion 609 to the translation motion 607 through selecting link configuration and lengths that linearize the rotation of joint 628 with translation 607, to allow use of a single motor or actuator to drive the proximal rotational motion 605, the translation motion 607, and the rotational motion 609. The input link 626b may be considered a bar B1. The coupler link 626c may be considered a bar B2. The distal linkage arm 616 between the distal joint 630 and the distal pivot joint 618 may be considered a bar B3. The translation linkage arm 614 between the distal pivot joint 618 and the joint 628 may be considered a bar B4. The bars B1-B4 form a closed-loop linkage. In some embodiments, the lengths of the bars B1-B4 may be selected for suitable operation of the 4-bar mechanism such that the rate of rotation of joint 628 to the rate of translation 607 are approximately linearized. The four-bar link configuration may be selected such that the angle and acceleration profile of the distal linkage arm 616 given a rotation of joint 628 proportional to the translation 607 maintains the RC position substantially unchanged for the kinematics and dynamics described. In some embodiments, a suitable ratio between the lengths of bar B1 and bar B4 is between approximately 3.1 and 5.6. In some embodiments, a suitable ratio between the lengths of bar B1 and bar B2 is between approximately 2.9 and 4.1. In some embodiments, a suitable ratio between the lengths of bar B1 and bar B3 is between approximately 1.3 and 2.3. In other embodiments, other ratios between the bar lengths may be suitable.

With reference again to FIG. 20, at a process 710, the instrument 621 rotates about the remote center of motion RC. More specifically, as the distal linkage arm 616 pivots about the distal pivot joint 618, the instrument 621, as well as the carriage and the cannula 620, which are attached to the distal linkage arm 616, each pivot about the remote center of motion RC. Optionally, the yaw joint may be driven via an actuation mechanism to rotate the base linkage arm 602 about the yaw axis to cause yaw motion to the manipulator assembly 600, as described above. The yaw motion may occur before, after, or concurrently with any of the processes 702 through 710.

In the embodiment of FIGS. 13-20, the single actuation mechanism 624 drives the proximal rotational motion 605, the translation motion 607 and the rotation motion 609. Thus, the relationships between the motions 605, 607, 609 maybe coupled and have a functional relationship relative to each other. In this embodiment, the actuation mechanism 624 may located in a proximal region of the manipulator 600 thus reducing the suspended weight of the linkage arms as compared to manipulators that locate the actuators proximate to the location of the joint or translational motion. In alternative embodiments where weight of the manipulator linkage arms may be less of a consideration, the distal pivot motion 609 may be driven not by the actuation mechanism 624, but by a separate actuation mechanism having a separate actuator such a motor.

One or more elements in embodiments of this disclosure may be implemented in software to execute on a processor of a computer system such as a control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus, and various systems may be used with programs in accordance with the teachings herein. The required structure for a variety of the systems discussed above will appear as elements in the claims. In addition, the embodiments of the invention are not described with reference to any particular programming language. It will be appreciated that a variety of programming languages may be used to implement the teachings of the invention as described herein.

In the above description, specific details describe some embodiments consistent with the present disclosure. Numerous specific details are set forth in order to provide a thorough understanding of the embodiments. It will be apparent to one skilled in the art, however, that some embodiments may be practiced without some or all of these specific details. The specific embodiments disclosed herein are meant to be illustrative but not limiting. One skilled in the art may realize other elements that, although not specifically described, are within the scope and the spirit of this disclosure. In addition, to avoid unnecessary repetition, one or more features shown and described in association with one embodiment may be incorporated into other embodiments unless specifically described otherwise or if the one or more features would make an embodiment non-functional. In some instances, well known methods, procedures, components, and circuits have not been described in detail so as not to unnecessarily obscure aspects of the embodiments.

In the above description, the singular forms "a", "an", and "the" are intended to include the plural forms as well, unless the context indicates otherwise. And the terms "comprises," "comprising," "includes," "has," and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components. The auxiliary verb "may" likewise implies that a feature, step, operation, element, or component is optional.

Although some of the examples described herein refer to surgical procedures or instruments, or medical procedures and medical instruments, the techniques disclosed optionally apply to non-medical procedures and non-medical instruments. For example, the instruments, systems, and methods described herein may be used for non-medical purposes including industrial uses, general robotic uses, and sensing or manipulating non-tissue work pieces. Other example applications involve cosmetic improvements, imaging of human or animal anatomy, gathering data from human or animal anatomy, and training medical or non-medical personnel. Additional example applications include use for procedures on tissue removed from human or animal anatomies (without return to a human or animal anatomy), and performing procedures on human or animal cadavers. Further, these techniques can also be used for surgical and nonsurgical medical treatment or diagnosis procedures.

Further, although some of the examples presented in this disclosure discuss teleoperational robotic systems or remotely operable systems, the techniques disclosed are also applicable to computer-assisted systems that are directly and manually moved by operators, in part or in whole.

Elements described in detail with reference to one embodiment, implementation, or application optionally may be included, whenever practical, in other embodiments, implementations, or applications in which they are not specifically shown or described. For example, if an element is described in detail with reference to one embodiment and is not described with reference to a second embodiment, the element may nevertheless be claimed as included in the second embodiment. Thus, to avoid unnecessary repetition in the following description, one or more elements shown and described in association with one embodiment, implementation, or application may be incorporated into other embodiments, implementations, or aspects unless specifically described otherwise, unless the one or more elements would make an embodiment or implementation non-functional, or unless two or more of the elements provide conflicting functions.

Various aspects of the subject matter described herein are set forth in the following numbered examples.

Example 1: A manipulator for articulating a surgical instrument, the manipulator comprising:
an instrument holder configured to couple with the surgical instrument and to pivot about a remote center of motion; and
a linkage assembly coupled to the instrument holder and configured to constrain rotational motion of the instrument holder to pivot about the remote center of motion, wherein the linkage assembly comprises:
a first linkage arm;
a second linkage arm rotatably coupled to the first linkage arm, wherein a proximal end of the first linkage arm and a proximal end of the second linkage arm are coupled at a proximal pivot joint; and
a third linkage arm translationally coupled to the second linkage arm, wherein movement of the second linkage arm and the third linkage arm causes a distal end of the third linkage arm to trace an arc around the remote center of motion.

Example 2. The manipulator of Example 1, further comprising:
a first actuator configured to drive translational motion of the third linkage arm relative to the second linkage arm, the first actuator further configured to drive pivotal motion of the second linkage arm relative to the first linkage arm about the proximal pivot joint.

Example 3. The manipulator of Example 2,
wherein the first linkage arm has a track, and
wherein the third linkage arm has a follower coupled to the track causing rotation of the second linkage arm relative to the first linkage arm about the proximal pivot joint.

Example 4. The manipulator of Example 3, further comprising a linear motion mechanism configured to drive the follower.

Example 5. The manipulator of Example 4, wherein the linear motion mechanism includes a ball screw comprising an elongated threaded shaft and a threaded nut, wherein the threaded nut is movably coupled to the elongated threaded shaft, and wherein the linear motion mechanism is driven by the first actuator.

Example 6. The manipulator of Example 5, wherein the follower is coupled to the threaded nut of the linear motion mechanism.

Example 7. The manipulator of Example 2, wherein the first actuator is housed within the second linkage arm and is pivotable along with the second linkage arm relative to the first linkage arm.

Example 8. The manipulator of Example 2, further comprising:
a fourth linkage arm rotatably coupled to the distal end of the third linkage arm at a first distal pivot joint, the fourth linkage arm being coupled to the instrument holder; and
a second actuator coupled to the third linkage arm to drive pivotal motion of the fourth linkage arm relative to the third linkage arm about the first distal pivot joint.

Example 9. The manipulator of Example 8, wherein the second actuator is housed within the third linkage arm and is translatable with the third linkage arm relative to the second linkage arm.

Example 10. The manipulator of Example 2, further comprising:
  a fourth linkage arm rotatably coupled to the distal end of the third linkage arm at a first distal pivot joint, the fourth linkage arm being coupled to the instrument holder; and
  a distal pivot motion mechanism coupling the first actuator and the fourth linkage arm, wherein the first actuator is configured to drive the fourth linkage arm via the distal pivot motion mechanism.

Example 11. The manipulator of Example 10, wherein the distal pivot motion mechanism includes a first link component pivotally coupled to the third linkage arm, a second link component pivotally coupled to the first link component and pivotally coupled to the fourth linkage arm, and a drive shaft with a proximal end coupled to the first actuator and a distal end rotationally coupled to the first link component.

Example 12. The manipulator of Example 11, wherein the drive shaft includes a worm gear section, and the first link component includes a set of teeth configured to engage the worm gear section, wherein rotation of the worm gear section by the first actuator causes the first link component to pivot relative to the third linkage arm.

Example 13. The manipulator of Example 12, further comprising:
  a follower to translationally couple movement of the third linkage arm to the second linkage arm; and
  a gear assembly coupled to the first actuator and configured to provide a first output to drive the distal pivot motion mechanism and a second output to drive the follower, wherein the first output has a different rotational speed than the second output.

Example 14. The manipulator of Example 13, wherein the second link component is coupled to the fourth linkage arm at a second distal pivot joint, the second distal pivot joint spaced apart from the first distal pivot joint.

Example 15. The manipulator of Example 14, wherein the second link component includes a recessed portion and wherein the first distal pivot joint is configured to extend into the recessed portion when the manipulator is in an extended configuration.

Example 16. The manipulator of Example 1, wherein the first linkage arm is rotationally coupled to a more proximal linkage at a yaw joint, the yaw joint configured to produce controlled rotation of the first linkage arm about a yaw axis that intersects the remote center of motion.

Example 17. A manipulator for articulating a surgical instrument, the manipulator comprising:
  an instrument holder configured to couple with the surgical instrument and to pivot through a remote center of motion; and
  a linkage assembly coupled to the instrument holder and configured to constrain motion of the instrument holder to pivot about the remote center of motion, wherein the linkage assembly comprises:
    a proximal pivot joint;
    a distal pivot joint; and
    an extension joint between the proximal pivot joint and the distal pivot joint,
    wherein a motor drives at least one of coupled motion of the proximal pivot joint and the extension joint and coupled motion of the extension joint and the distal pivot joint.

Example 18. The manipulator of Example 17, further comprising:
  the motor.

Example 19. A manipulator for articulating a surgical instrument, the manipulator comprising:
  an instrument holder configured to couple with the surgical instrument and to pivot about a remote center of motion; and
  a linkage assembly coupled to the instrument holder and configured to constrain motion of the instrument holder to pivot about the remote center of motion, wherein the linkage assembly comprises:
    a first linkage arm having a guide;
    a second linkage arm rotatably coupled to the first linkage arm; and
    a third linkage arm translationally coupled to the second linkage arm and configured to travel along the guide of the first linkage arm, wherein movement of the second linkage arm and the third linkage arm cause a distal end of the third linkage arm to trace an arc around the remote center of motion.

Example 20. The manipulator of Example 19, wherein the third linkage arm includes a follower coupled to the track causing rotation of the second linkage arm relative to the first linkage arm.

Example 21. The manipulator of Example 20, further comprising a linear motion mechanism configured to drive the follower.

Example 22. The manipulator of Example 21, wherein the linear motion mechanism includes a ball screw comprising an elongated threaded shaft and a threaded nut, wherein the threaded nut is movably coupled to the elongated threaded shaft.

Example 23. The manipulator of Example 22, wherein the follower is coupled to the threaded nut of the linear motion mechanism.

Example 24. The manipulator of Example 23, further comprising a fourth linkage arm rotatably coupled to a distal end of the third linkage arm, the fourth linkage arm being coupled to the instrument holder.

Example 25. A method of operating a manipulator including a translation linkage arm, a pivot linkage arm and a base linkage arm, the method comprising:
  translating the translation linkage arm relative to the pivot linkage arm and the base linkage arm, wherein the base linkage arm includes a guide, wherein a follower coupled to the translation linkage arm is configured to move within the track of the base linkage arm, wherein the pivot linkage arm is coupled to the base linkage arm by a proximal pivot joint;
  pivoting the pivot linkage arm and the translation linkage arm relative to the base linkage arm about the proximal pivot joint as the follower moves within the guide of the base linkage arm;
  tracing an arc around a remote center of motion of the manipulator with a distal end of the translation linkage arm; and
  rotating an instrument holder about the remote center of motion of the manipulator.

Example 26. The method of Example 25, wherein the guide has a curvilinear shaped path and wherein moving the follower along the curvilinear shaped path causes the translating of the translation linkage arm relative to the pivot linkage arm and causes the pivoting of the pivot linkage arm and the translation linkage arm relative to the base linkage arm.

Example 27. The method of Example 25, further comprising:
  actuating a first actuator coupled to the follower to translate the translation linkage arm relative to the pivot linkage arm and the base linkage arm and to pivot the pivot linkage arm and the translation linkage arm about the proximal pivot joint.

Example 28. The method of Example 27, wherein actuating the first actuator comprises driving a linear motion mechanism coupling the first actuator and the follower.

Example 29. The method of Example 28, wherein driving the linear motion mechanism includes moving a threaded nut along an elongated threaded shaft.

Example 30. The method of Example 29, wherein the follower is coupled to the threaded nut of the linear motion mechanism and wherein driving the linear motion mechanism includes moving the follower relative to the elongated threaded shaft.

Example 31. The method of Example 28, wherein the linear motion mechanism includes a carriage movably coupled to a track and wherein driving the linear motion mechanism includes moving the carriage along the track.

Example 32. The method of Example 31, wherein the follower is coupled to the carriage of the linear motion mechanism and wherein driving the linear motion mechanism includes moving the follower along the track.

Example 33. The method of Example 27, wherein the first actuator is housed within the pivot linkage arm and wherein pivoting the pivot linkage arm includes pivoting the first actuator relative to the base linkage arm.

Example 34. The method of Example 27, further comprising:
  pivoting a distal linkage arm relative to the translation linkage arm, wherein the distal linkage arm is coupled to a distal end of the translation linkage arm by a first distal pivot joint and wherein the instrument holder is rigidly coupled to the distal linkage arm and pivots about the remote center of motion of the manipulator; and
  actuating a second actuator coupled to the translation linkage arm to drive the pivoting of the distal linkage arm relative to the translation linkage arm about the first distal pivot joint.

Example 35. The method of Example 34, wherein actuating the second actuator includes moving a distal pivot motion mechanism coupled between the second actuator and the distal linkage arm.

Example 36. The method of Example 35, wherein the distal pivot motion mechanism includes a ball screw comprising an elongated threaded shaft, a threaded nut coupled to the elongated threaded shaft, and an auxiliary linkage arm with a proximal end coupled to the threaded nut and a distal end coupled to the distal linkage arm and wherein moving the distal pivot motion mechanism includes moving the threaded nut along the elongated threaded shaft.

Example 37. The method of Example 34, wherein the second actuator is housed within the translation linkage arm and is translatable with the translation linkage arm relative to the pivot linkage arm.

Example 38. The method of Example 37, further comprising:
  pivoting a distal linkage arm relative to the translation linkage arm, wherein the distal linkage arm is coupled to a distal end of the translation linkage arm by a first distal pivot joint, wherein the instrument holder is rigidly coupled to the distal linkage arm and pivots about the remote center of motion of the manipulator, and wherein a distal pivot motion mechanism couples the first actuator and the distal linkage arm.

Example 39. The method of Example 38, wherein the distal pivot motion mechanism includes a first link component pivotally coupled to the translation linkage arm, a second link component pivotally coupled to the first link component and pivotally coupled to the distal linkage arm, and a drive shaft with a proximal end coupled to the first actuator and a distal end rotationally coupled to the first link component and wherein actuating the first actuator causes motion of the distal pivot motion mechanism relative to the translation linkage arm.

Example 40. The method of claim Example 39, wherein the drive shaft includes a worm gear section and the first link component includes a set of teeth configured to engage the worm gear section, and actuating the first actuator causes rotation of the worm gear section to drive the first link component to pivot relative to the translation linkage arm.

Example 41. The method of Example 39, wherein a gear assembly is coupled to the first actuator and provides a first output to drive the distal pivot motion mechanism and a second output to drive the follower, where in the first output has a different rotational speed than the second output.

What is claimed is:

1. A manipulator for articulating a surgical instrument, the manipulator comprising:
  an instrument holder configured to couple with the surgical instrument and to pivot about a remote center of motion; and
  a linkage assembly coupled to the instrument holder and configured to constrain rotational motion of the instrument holder to pivot about the remote center of motion, wherein the linkage assembly comprises:
    a first linkage arm;
    a second linkage arm rotatably coupled to the first linkage arm, wherein a proximal end of the first linkage arm and a proximal end of the second linkage arm are coupled at a proximal pivot joint; and
    a third linkage arm coupled to and translationally movable relative to the second linkage arm without rotation of the third linkage arm relative to the second linkage arm, wherein movement of the second linkage arm and the third linkage arm causes a distal end of the third linkage arm to trace an arc around the remote center of motion.

2. The manipulator of claim 1, further comprising:
  a first actuator configured to drive translational motion of the third linkage arm relative to the second linkage arm, the first actuator further configured to drive pivotal motion of the second linkage arm relative to the first linkage arm about the proximal pivot joint.

3. The manipulator of claim 2,
  wherein the first linkage arm has a track, and
  wherein the third linkage arm has a follower coupled to the track causing rotation of the second linkage arm relative to the first linkage arm about the proximal pivot joint.

4. The manipulator of claim 3, wherein the track has a curvilinear shape.

5. The manipulator of claim 3, further comprising a linear motion mechanism configured to drive the follower.

6. The manipulator of claim 2, further comprising:
  a fourth linkage arm rotatably coupled to the distal end of the third linkage arm at a first distal pivot joint, the fourth linkage arm being coupled to the instrument holder; and a second actuator coupled to the third linkage arm to drive pivotal motion of the fourth linkage arm relative to the third linkage arm about the first distal pivot joint.

7. The manipulator of claim 6, further comprising:
a distal pivot motion mechanism coupling the second actuator and the fourth linkage arm.

8. The manipulator of claim 7, wherein the distal pivot motion mechanism includes a ball screw comprising an elongated threaded shaft, a threaded nut movably coupled to the elongated threaded shaft and driven by the second actuator, and a fifth linkage arm with a proximal end coupled to the threaded nut and a distal end coupled to the fourth linkage arm.

9. The manipulator of claim 2, further comprising:
a fourth linkage arm rotatably coupled to the distal end of the third linkage arm at a distal pivot joint, the fourth linkage arm being coupled to the instrument holder; and
a distal pivot motion mechanism coupling the first actuator and the fourth linkage arm, wherein the first actuator is configured to drive the fourth linkage arm via the distal pivot motion mechanism.

10. The manipulator of claim 2, wherein the proximal pivot joint, the distal pivot joint, and a translational movement of the third linkage arm are each driven by separate actuators.

11. A manipulator for articulating a surgical instrument, the manipulator comprising:
an instrument holder configured to couple with the surgical instrument and to pivot through a remote center of motion; and
a linkage assembly coupled to the instrument holder and configured to constrain motion of the instrument holder to pivot about the remote center of motion, wherein the linkage assembly comprises:
a proximal pivot joint;
a distal pivot joint; and
an extension joint coupling a pair of linkage arms between the proximal pivot joint and the distal pivot joint, the extension joint configured to move a first arm of a pair of linkage arms translationally relative to a second arm of the pair of linkage arms without rotation of the first arm relative to the second arm,
wherein a motor drives at least one of coupled motion of the proximal pivot joint and the extension joint and coupled motion of the extension joint and the distal pivot joint.

12. The manipulator of claim 11, wherein the motor drives coupled motion of the extension joint, the proximal pivot joint, and the distal pivot joint.

13. The manipulator of claim 11, wherein the extension joint is configured to restrict rotational motion.

14. The manipulator of claim 11, wherein the linkage assembly includes a first linkage arm coupled to a second linkage arm at the proximal pivot joint, wherein the second linkage arm is the second arm of the pair of linkage arms.

15. The manipulator of claim 14, wherein the second linkage arm is rotatably coupled to the first linkage arm, wherein a proximal end of the first linkage arm and a proximal end of the second linkage arm are coupled at the proximal pivot joint.

16. The manipulator of claim 15, wherein the linkage assembly further includes a third linkage arm translationally coupled to the second linkage arm, wherein the third linkage arm is the first arm of the pair of linkage arms, wherein movement of the second linkage arm and the third linkage arm causes a distal end of the third linkage arm to trace an arc around the remote center of motion.

17. A manipulator for articulating a surgical instrument, the manipulator comprising:
an instrument holder configured to couple with the surgical instrument and to pivot about a remote center of motion; and
a linkage assembly coupled to the instrument holder and configured to constrain motion of the instrument holder to pivot about the remote center of motion, wherein the linkage assembly comprises:
a first linkage arm having a guide;
a second linkage arm rotatably coupled to the first linkage arm; and
a third linkage arm coupled to and translationally movable relative to the second linkage arm without rotation of the third linkage arm relative to the second linkage arm, wherein the third linkage arm is configured to travel along the guide of the first linkage arm, and wherein movement of the second linkage arm and the third linkage arm cause a distal end of the third linkage arm to trace an arc around the remote center of motion.

18. The manipulator of claim 17, wherein the guide includes track with a curvilinear shape.

19. The manipulator of claim 18, wherein the third linkage arm includes a follower coupled to the track causing rotation of the second linkage arm relative to the first linkage arm.

20. The manipulator of claim 19, further comprising a linear motion mechanism configured to drive the follower.

* * * * *

UNITED STATES PATENT AND TRADEMARK OFFICE
CERTIFICATE OF CORRECTION

PATENT NO. : 12,343,103 B2  
APPLICATION NO. : 17/540396  
DATED : July 1, 2025  
INVENTOR(S) : Ashley Lynne Oliver et al.

Page 1 of 1

It is certified that error appears in the above-identified patent and that said Letters Patent is hereby corrected as shown below:

In the Specification

Column 18, Line 12, change "it-rocker" to -- π-rocker --.

Signed and Sealed this
Nineteenth Day of August, 2025

Coke Morgan Stewart
*Acting Director of the United States Patent and Trademark Office*